United States Patent
Pajvani

(10) Patent No.: US 10,801,068 B2
(45) Date of Patent: Oct. 13, 2020

(54) JAG1 EXPRESSION PREDICTS THERAPEUTIC RESPONSE IN NASH

(71) Applicant: Utpal Pajvani, Leonia, NJ (US)

(72) Inventor: Utpal Pajvani, Leonia, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 40 days.

(21) Appl. No.: 15/768,701

(22) PCT Filed: Oct. 14, 2016

(86) PCT No.: PCT/US2016/057166
§ 371 (c)(1),
(2) Date: Apr. 16, 2018

(87) PCT Pub. No.: WO2017/066659
PCT Pub. Date: Apr. 20, 2017

(65) Prior Publication Data
US 2018/0298443 A1      Oct. 18, 2018

Related U.S. Application Data

(60) Provisional application No. 62/242,888, filed on Oct. 16, 2015.

(51) Int. Cl.
*C12Q 1/6883*  (2018.01)
*C12Q 1/68*    (2018.01)
*G01N 33/50*   (2006.01)

(52) U.S. Cl.
CPC ............ *C12Q 1/6883* (2013.01); *C12Q 1/68* (2013.01); *G01N 33/5023* (2013.01); *C12Q 2600/106* (2013.01); *C12Q 2600/118* (2013.01); *C12Q 2600/158* (2013.01); *G01N 2333/70596* (2013.01); *G01N 2800/52* (2013.01)

(58) Field of Classification Search
CPC ..... G01N 33/5023; C12Q 1/68; C12Q 1/6883
See application file for complete search history.

(56) References Cited

U.S. PATENT DOCUMENTS

| | | |
|---|---|---|
| 8,889,660 B2 | 11/2014 | Palczewski et al. |
| 2010/0008899 A1 | 1/2010 | Williams |
| 2011/0039766 A1 | 2/2011 | Szeto |
| 2013/0019326 A1 | 1/2013 | Spiegelman et al. |
| 2013/0219534 A1 | 8/2013 | Wong et al. |
| 2014/0099326 A1 | 4/2014 | Schmidt et al. |

OTHER PUBLICATIONS

Chalasani et al., The Diagnosis and Management of Non-Alcoholic Fatty Liver Disease: Practice Guideline by the American Association for the Study of Liver Diseases, American College of Gastroenterology, and the American Gastroenterological Association; Hepatology, vol. 55, No. 6, 2012, pp. 2005-2023 (Year: 2012).*

Takahashi et al.; Current pharmacological therapies for nonalcoholic fatty liver disease/nonalcoholic steatohepatitis; World Journal of Gastroenterology; vol. 21, No. 13, pp. 3777-3785, Apr. 7, 2015 (Year: 2015).*

Bayard et al.; Nonalcoholic Fatty Liver Disease; American Family Physician, vol. 73, No. 11, pp. 1961-1968; Jun. 1, 2006 (Year: 2006).*

International Search Report dated Jan. 10, 2017 in connection with PCT International Application No. PCT/US2016/057166.

Written Opinion of the International Searching Authority dated Jan. 10, 2017 in connection with PCT International Application No. PCT/US2016/057166.

* cited by examiner

*Primary Examiner* — Antonio Galisteo Gonzalez
(74) *Attorney, Agent, or Firm* — John P. White; Gary J. Gershik; Cooper & Dunham LLP

(57) ABSTRACT

The present invention provides a method for treating a human subject afflicted with a metabolic disease with a pharmaceutical composition, comprising the steps of: (i) determining JAG1 expression level in the subject; (ii) identifying the subject as a predicted responder if JAG1 expression level is greater than 1.5 fg/ng 18S; and (iii) administering the pharmaceutical composition to the subject only if the subject is identified as a predicted responder.

14 Claims, 12 Drawing Sheets

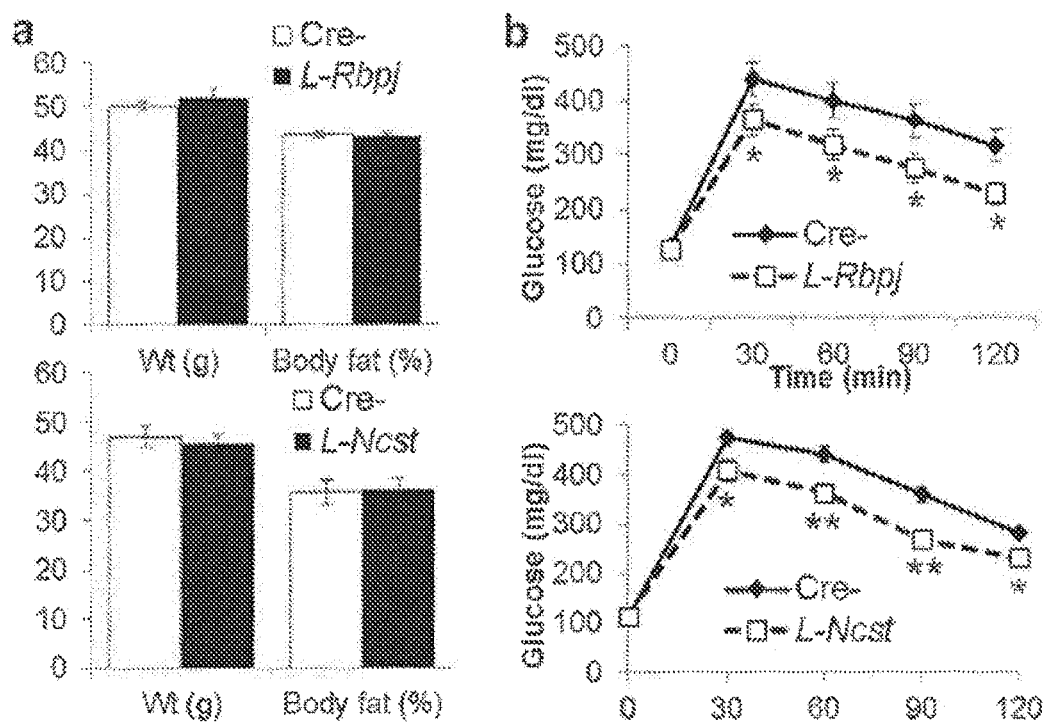
FIGS. 1A-B

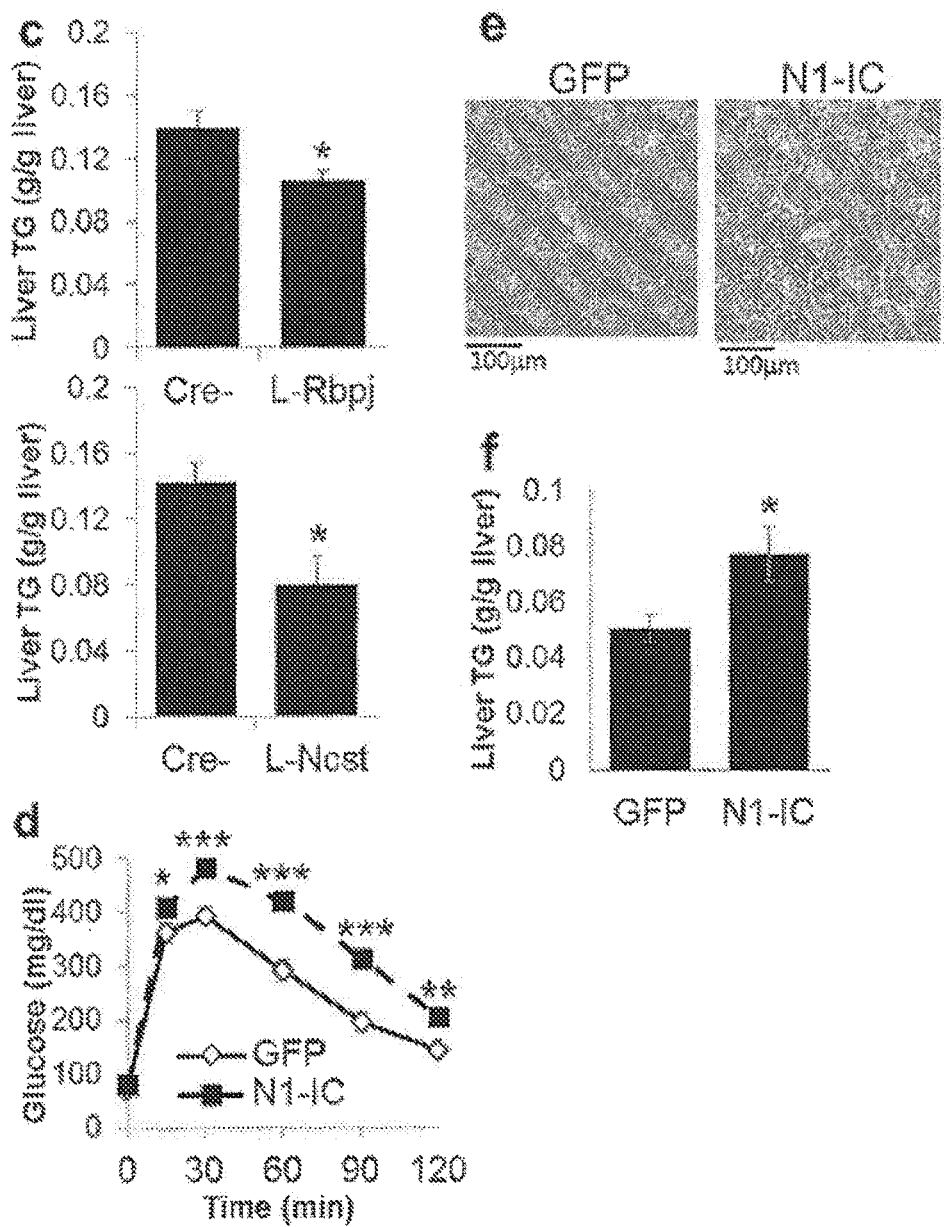
FIGS. 1C-F

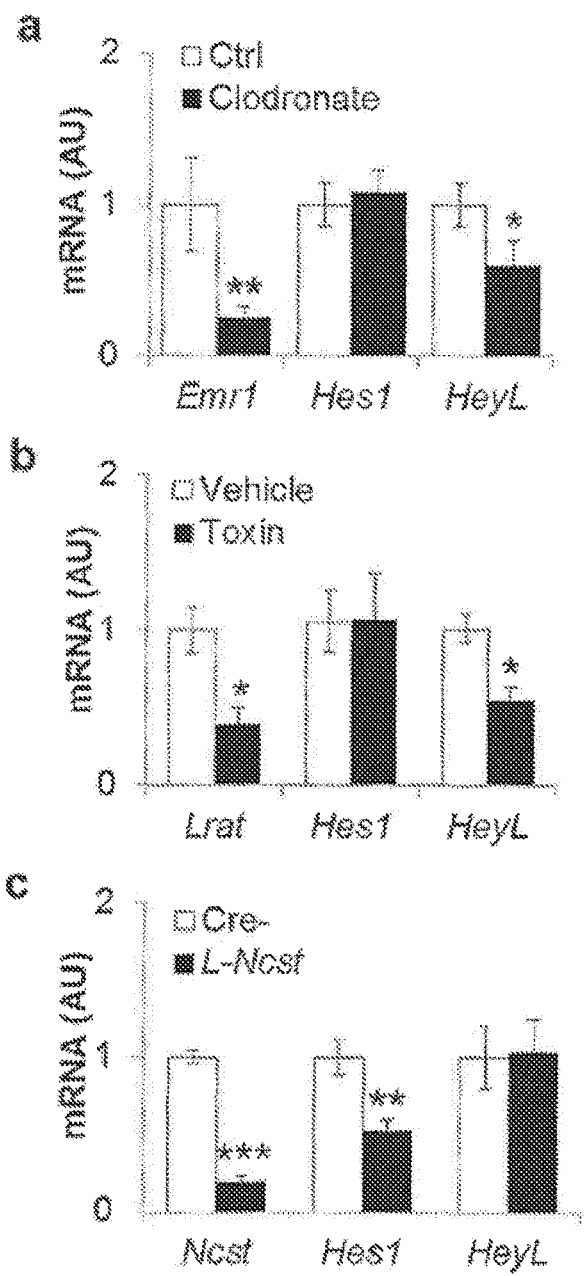
FIGS. 3A-C

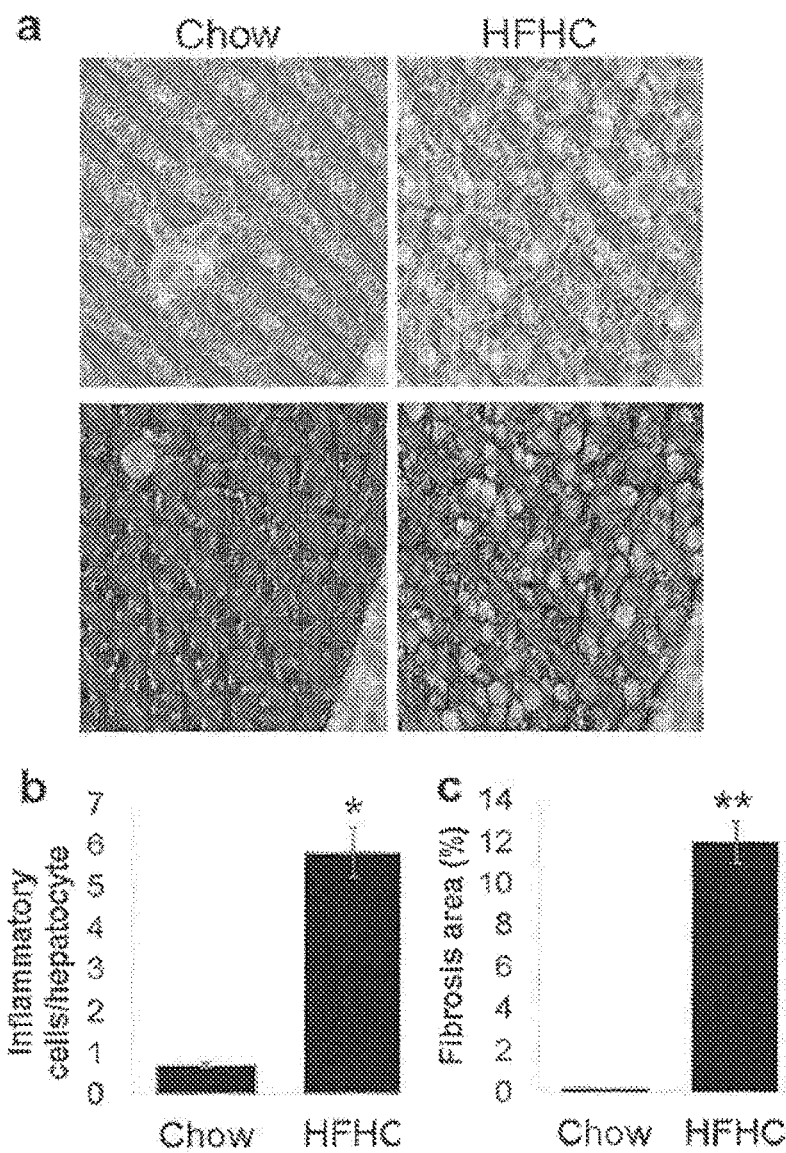
FIGS. 4A-C

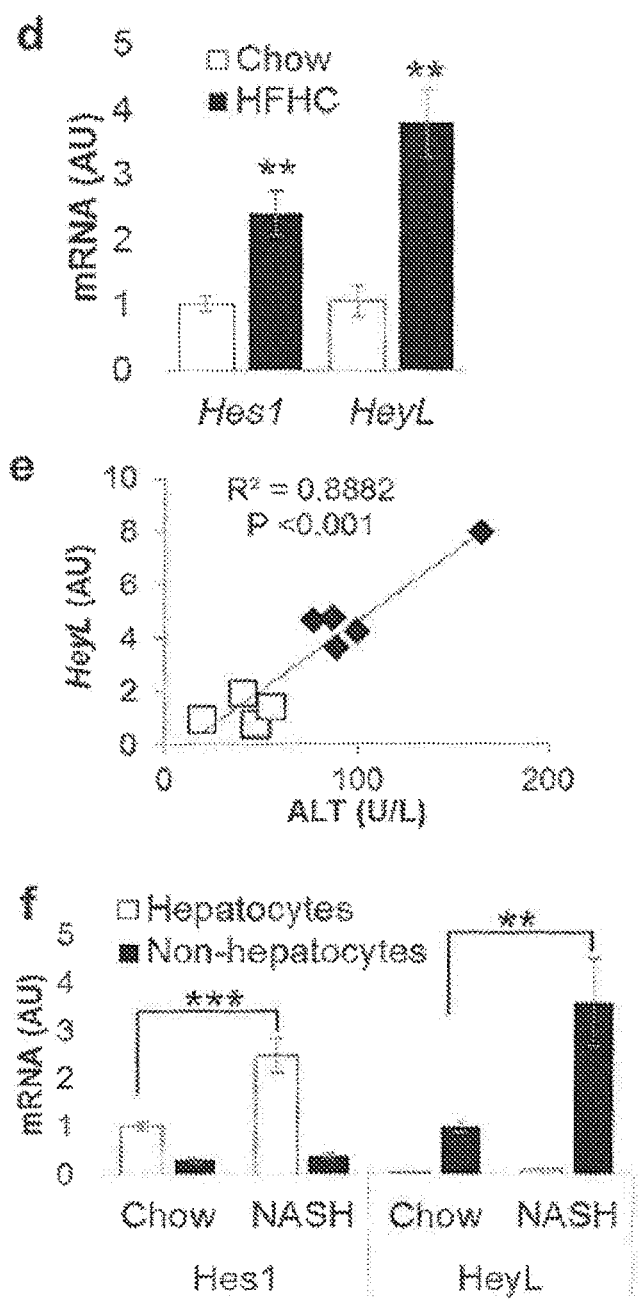
FIGS. 4D-F

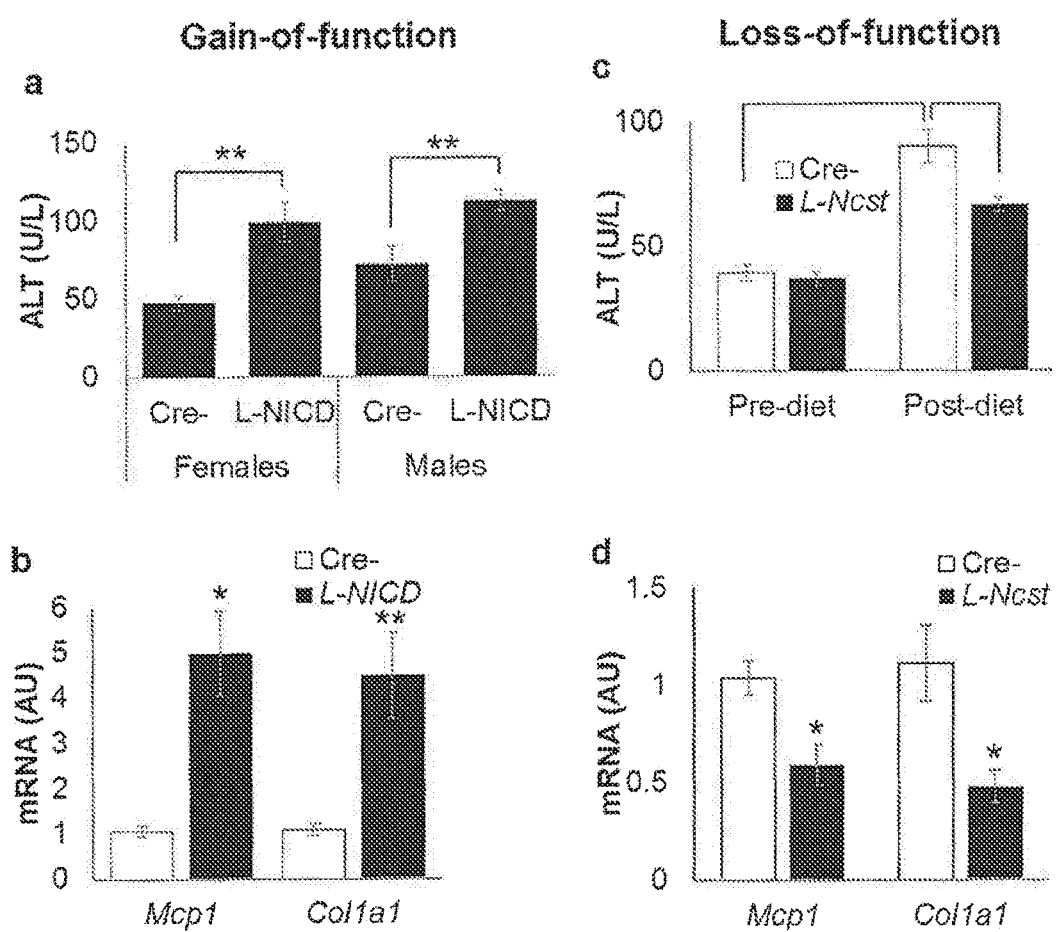
FIGS. 5A-D

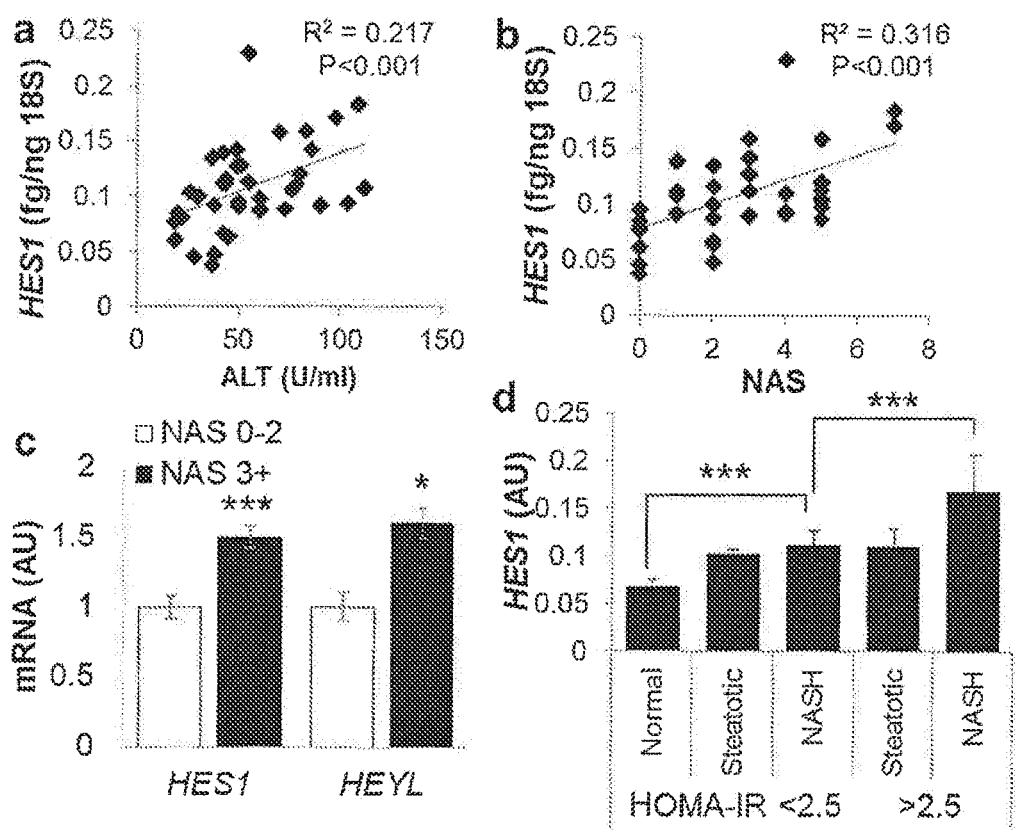
FIGS. 6A-D

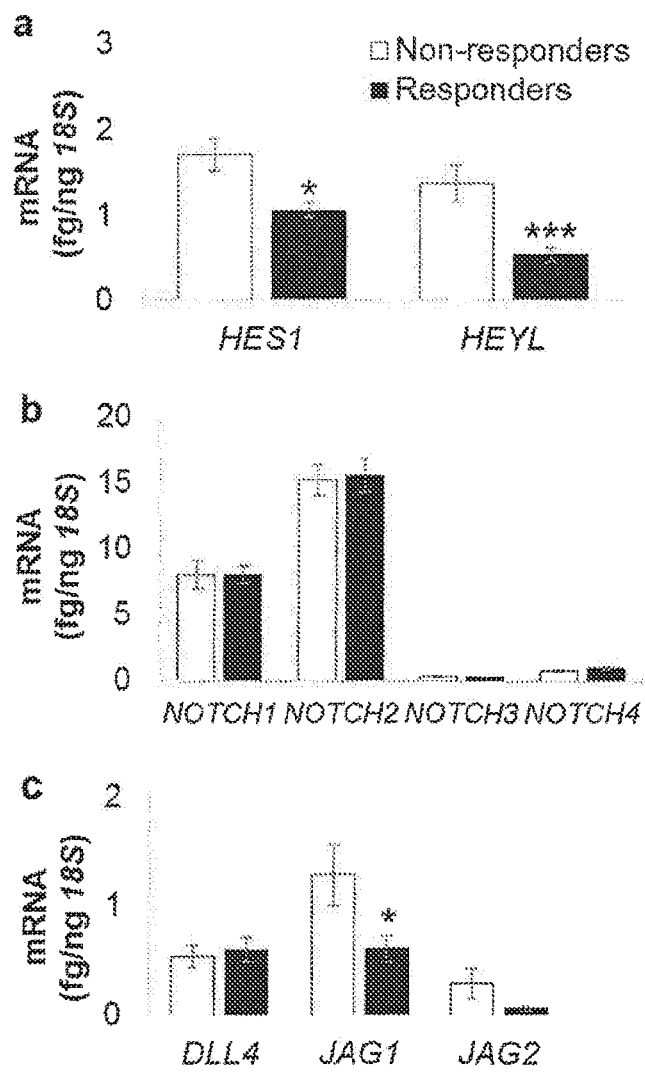
FIGS. 7A-C

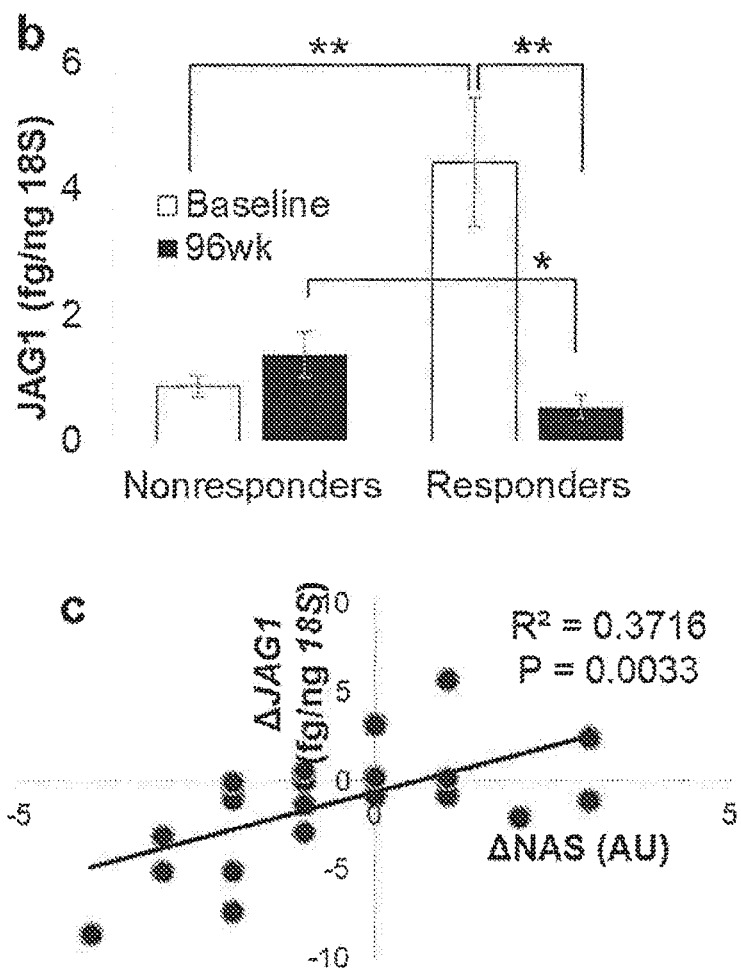
FIGS. 8B-C

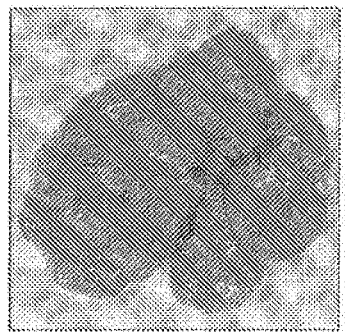
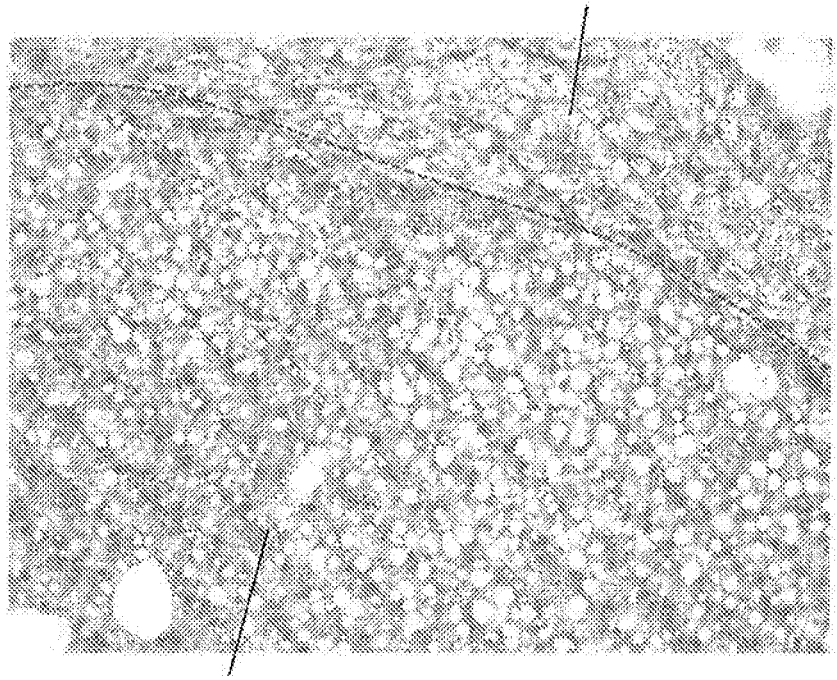
FIGS. 9A-B

JAG1 EXPRESSION PREDICTS THERAPEUTIC RESPONSE IN NASH

This application is a § 371 national stage of PCT International Application No. PCT/US2016/057166, filed Oct. 14, 2016 and claims the benefit of U.S. Provisional Application No. 62/242,888, filed Oct. 16, 2015, the contents of each of which are hereby incorporated by reference in their entirety.

Throughout this application various publications are referenced by numerical identifiers in parentheses. Full citations of these references can be found following the Examples. The disclosures of these publications in their entireties are hereby incorporated by reference into this application in order to more fully describe the state of the art to which this invention pertains.

This invention was made with government support under grant DK105303 awarded by the National Institutes of Health. The government has certain rights in the invention.

BACKGROUND OF THE INVENTION

Obesity manifests as multiple pathologic states in liver. Insulin resistance in adipocytes results in unrestrained lipolysis, with consequent excess free fatty acid flux to the liver (Savage and Semple 2010). In a parallel pathogenic process, excess adiposity leads to insulin resistance, which begets the fasting hyperglycemia of Type 2 diabetes (T2D) (Lin and Accili 2011). Compensatory hyperinsulinemia drives hepatic de novo lipogenesis mediated by the nutrient-sensitive mechanistic target of rapamycin (mTOR) pathway (Li, Brown et al. 2010), and coupled with an impaired ability to catabolize and export fatty acids (Bugianesi, Gastaldelli et al. 2005), results in excess hepatocyte triglyceride accumulation, or non-alcoholic fatty liver disease (NAFLD). As both the prevalence of obesity and the frequency of imaging studies increase, the clinical diagnosis of the excess hepatic fat that defines NAFLD is increasingly common (Bhala, Jouness et al. 2013, Dongiovanni, Anstee et al. 2013). NAFLD prevalence is increasing in parallel with increased obesity. In data from the National Health and Nutrition Examination Survey (NHANES), prevalence of nonalcoholic fatty liver disease (NAFLD) in the United States population has increased from 5.5% in 1988 to 11% in 2008 and is now the leading cause of chronic liver disease in the United States (Younossi, Stepanova et al. 2011).

NAFLD ranges in severity from simple (benign) steatosis, to hepatocellular damage and necroinflammatory changes which define non-alcoholic steatohepatitis (NASH). NASH is a pathological diagnosis made at liver biopsy. Regrettably, this progression of NAFLD, a potential "pre-disease" state with prevalence approaching 30% in some populations (Bhala, Jouness et al. 2013), to NASH, which predisposes to cirrhosis and need for liver transplantation, is unpredictable for any given patient (Loria, Adinolfi et al. 2010). In fact, the majority of patients diagnosed with excess hepatic fat will never develop NASH (Bhala, Jouness et al. 2013). The transition between NAFLD and NASH has an inadequately defined molecular signature, and biomarkers proposed to noninvasively monitor the NAFLD-NASH progression have not proven to be mechanistic determinants of the process (Hashimoto and Farrell 2009, Malik, Chang et al. 2009). Recent work suggests a "multiple-hit" hypothesis, (Tilg 2010)[11-14] where the first hit of fat accumulation sensitizes the liver to further injury, mediated by cross-talk between hepatocytes and other liver residents to accelerate a fairly benign process to one that has severe clinical consequence without approved pharmacologic therapy (Hashimoto 2009).[10,15] Available livers for transplantation will not keep pace with the expected growth in NASH over the next few decades—novel pathways are sought to both further our understanding of the pathophysiology of NAFLD/NASH as well as provide potential new pharmaceutical targets to assist in our management of obesity-related morbidity and mortality.

The problem of obesity is a metabolic toxicity that causes morbidity and mortality. Type 2 Diabetes and NAFLD are synergistic contributors to cardiovascular risk. Type 2 Diabetes is a leading cause of blindness and end-stage renal disease and dialysis. To date, Type 2 Diabetes is inadequately treated with current therapies.

There is a staggering rise in prevalence of obesity and its complications, with wideranging impact. Existing and novel therapeutics that target the complications of obesity, including fatty liver (the most frequent cause of chronic liver disease, and the fastest growing reason for liver transplantation), are necessary to combat this growing problem, but clinical efficacy of these therapeutics is variable. A clinical predictor of treatment success would be invaluable to solve this problem.

SUMMARY OF THE INVENTION

The present invention provides a method for treating a human subject afflicted with a metabolic disease with a pharmaceutical composition, comprising the steps of:
  i) determining JAG1 expression level in the subject;
  ii) identifying the subject as a predicted responder if JAG1 expression level is greater than 1.5 fg/ng 18S; and
  iii) administering the pharmaceutical composition to the subject only if the subject is identified as a predicted responder.

The present invention also provides a method of identifying a human subject afflicted with a metabolic disease as a predicted responder or as a predicted non-responder to a pharmaceutical composition, the method comprising determining JAG1 expression level in the subject and identifying the human subject as a predicted responder to the pharmaceutical composition if the JAG1 expression level is greater than 1.5 fg/ng 18S, or identifying the human subject as a predicted non-responder to the pharmaceutical composition if the JAG1 expression level is less than 1.0 fg/ng 18S.

The present invention also provides a method of predicting clinical responsiveness to a pharmaceutical composition in a human subject afflicted with metabolic disease, the method comprising evaluating JAG1 expression level in the subject, to thereby predict clinical responsiveness to the pharmaceutical composition.

The present invention also provides a method for treating a human subject afflicted with a metabolic disease with a pharmaceutical composition, comprising the steps of:
  i) determining whether the human subject is a responder to the pharmaceutical composition by evaluating JAG1 expression level in the subject; and
  ii) administering the pharmaceutical composition to the subject only if the subject is identified as a predicted responder.

The present invention also provides a kit for identifying a human subject afflicted with a metabolic disease as a predicted responder or as a predicted non-responder to a pharmaceutical composition, the kit comprising at least one probe specific for JAG1 and at least one probe specific for 18S in the sample.

The present invention also provides a kit for identifying a human subject afflicted with a metabolic disease as a predicted responder or as a predicted non-responder to a pharmaceutical composition, the kit comprising at least one PCR primer designed to amplify a DNA segment specific for JAG1 and at least one PCR primer specific for 18S in the sample.

The present invention also provides a method for treating a human subject afflicted with a metabolic disease with a pharmaceutical composition, comprising the steps of:
 i) determining JAG1 expression level in the subject;
 ii) determining HES1 expression level in the subject;
 iii) identifying the subject as a predicted responder if the JAG1 expression level is greater than 1.5 fg/ng 18S, and the HES1 expression level is greater than 1.0 fg/ng 18S; and
 iv) administering the pharmaceutical composition to the subject only if the subject is identified as a predicted responder.

The present invention also provides a method of identifying a human subject afflicted with a metabolic disease as a predicted responder or as a predicted non-responder to a pharmaceutical composition, the method comprising determining JAG1 and HES1 expression levels of the subject and identifying the human subject as a predicted responder to the pharmaceutical composition if the JAG1 expression level is greater than 1.5 fg/ng 18S, and the HES1 expression level is greater than 1.0 fg/ng 18S, or identifying the human subject as a predicted non-responder to the pharmaceutical composition if the JAG1 expression level is less than 1.5 fg/ng 18S and the HES1 expression level is less than 1.0 fg/ng 18S.

The present invention also provides a method of predicting clinical responsiveness to a pharmaceutical composition in a human subject afflicted with metabolic disease, the method comprising evaluating JAG1 and HES1 expression levels in the subject, to thereby predict clinical responsiveness to the pharmaceutical composition.

The present invention also provides a method for treating a human subject afflicted with a metabolic disease with a pharmaceutical composition, comprising the steps of:
 i) determining whether the human subject is a responder to the pharmaceutical composition by evaluating JAG1 and HES1 expression levels in the subject; and
 ii) administering the pharmaceutical composition to the subject only if the subject is identified as a predicted responder.

The present invention also provides a method for treating a human subject afflicted with a metabolic disease with a pharmaceutical composition, comprising the steps of:
 i) determining JAG1 expression level in the subject;
 ii) determining HES1 expression level in the subject;
 iii) determining HEYL expression level in the subject;
 iv) identifying the subject as a predicted responder if the JAG1 expression level is greater than 1.5 fg/ng 18S, the HES1 expression level is greater than 1.5 fg/ng 18S, and the HEYL expression level is greater than 1.5 fg/ng 18S; and
 v) administering the pharmaceutical composition to the subject only if the subject is identified as a predicted responder.

The present invention also provides a method of identifying a human subject afflicted with a metabolic disease as a predicted responder or as a predicted non-responder to a pharmaceutical composition, the method comprising determining JAG1, HES1, and HEYL expression levels in the subject and identifying the human subject as a predicted responder to the pharmaceutical composition if JAG1 expression level is greater than 1.5 fg/ng 18S, HES1 expression level is greater than 1.5 fg/ng 18S, and HEY1 expression level is greater than 1.5 fg/ng 18S, or identifying the human subject as a predicted non-responder to the pharmaceutical composition if the JAG1 expression level is less than 1.0 fg/ng 18S, the HES1 expression level is less than 1.5 fg/ng 18S, and the HEYL expression level is less than 1.5 fg/ng 18S.

The present invention also provides a method of predicting clinical responsiveness to a pharmaceutical composition in a human subject afflicted with metabolic disease, the method comprising evaluating JAG1, HES1, and HEYL expression levels in the subject, to thereby predict clinical responsiveness to the pharmaceutical composition.

The present invention also provides a method for treating a human subject afflicted with a metabolic disease with a pharmaceutical composition, comprising the steps of:
 i) determining whether the human subject is a responder to the pharmaceutical composition by evaluating JAG1, HES1, and HEYL expression levels in RNA isolated from the human subject's liver cells; and
 ii) administering the pharmaceutical composition to the subject only if the subject is identified as a predicted responder.

BRIEF DESCRIPTION OF THE DRAWINGS

FIGS. 1A-F. Notch is necessary and sufficient to induce obesity-induced glucose intolerance and fatty liver. Despite unchanged body weit and adiposity (A), HFD-led L-Rbpj (top panels) and L-ncst (bottom panels) mice show (B) improved glucose tolerance and (C) decrease liver triglyceride (TG). Conversely, adenoviral transduction of N1-IC induces (D) glucose intolerance and (E) hepatic steatosis (by Oil-Red-O staining), (F) due to excess liver TG, even in chow-fed mice. $*p<0.05$, $p<0.01$ and $*p<0.001$ as compared to Cre- or GFP-transduced controls.

FIGS. 3A-C. Markers of Notch activity and different hepatocytes and non-hepatocyes. Liver gene expression in chow-fed (A) WT mice injected with liposomal clodronate to deplete phagocytic cells (or empty liposomes, Ctrl), (B) Lrat-cre:DTR$^{f/f}$ mice treated with vehicle or diphtheria toxin, and (C) Cre- and L-ncst mice.

FIGS. 4A-F. HFHC-feeding induces liver injury and Notch activity. (A) Liver H+E (top) and Trichrome (bottom) staining, with (B) quantitation of inflammatory cells and (C) fibrosis area, and measurement of (D) hepatic gene expression, (E) expressed in relation to plasma ALT in HFHC-fed WT mice. (F) Notch gene expression in isolated hepatocytes and non-hepatocytes from Chow or HFHC-fed mice. $*p<0.05$, $p<0.01$ and $*p<0.001$ as compared to indicated control.

FIGS. 5A-D. Notch activation exacerbates hepatic inflammation and fibrosis. (A) ALT levels and (B) hepatic gene expression in HFHC-fed Cre- and L-NICD mice (C) ALT levels from male Cre- and L-Ncst mice before and after 16 wk of HFHC-feeding. (D) hepatic gene expression in HFHC-fed Cre- and L-Ncst mice. $*p<0.05$, $p<0.01$, and $*p<0.001$ as compared to indicated controls.

FIGS. 6A-D. Notch activity in liver increase with NASH. (A) Liver HES1 expression correlates with plasma ALT levels and (B) NAS score. (C) Notch activity is highest in patients with NAFLD Activity Score (NAS)>2 and (D) in patients with coincident NASH and insulin resistance (HOMA-IR>2.5). $*p<0.05$, $p<0.01$, and $*p<0.001$ as compared to NAS 0-2.

FIGS. 7A-C. Lower Notch activity and JAG1 expression in PIVENS responders. (A) Liver Notch target, (B) receptor and (C) ligand expression in patients who achieved the primary PIVENS outcome or had NASH resolution ("responder"), as compared to "non-responders". *$p<0.05$, $p<0.01$, and *$p<0.001$ as compared to non-responders.

FIGS. 8A-C. Higher baseline Notch activity predicts therapeutic response in PIVENS. (A) Baseline and end-of-treatment (96 wk) liver HES1/HEYL and (B) JAG1 expression in PIVENS nonresponders and responders, and (C) scatter plot of change in JAG1 expression from baseline to 96 wk (ΔNAS). *$p<0.05$, **$p<0.01$ as compared to indicated control.

FIGS. 9A-B. Notch causes NASH-induced hepatocellular carcinoma (HCC). (A) Liver biopsy. (B) Neo-neoplastic liver and liver neoplasm resembling human HCC.

DETAILED DESCRIPTION OF THE INVENTION

Embodiments of the Invention

Figure 2:
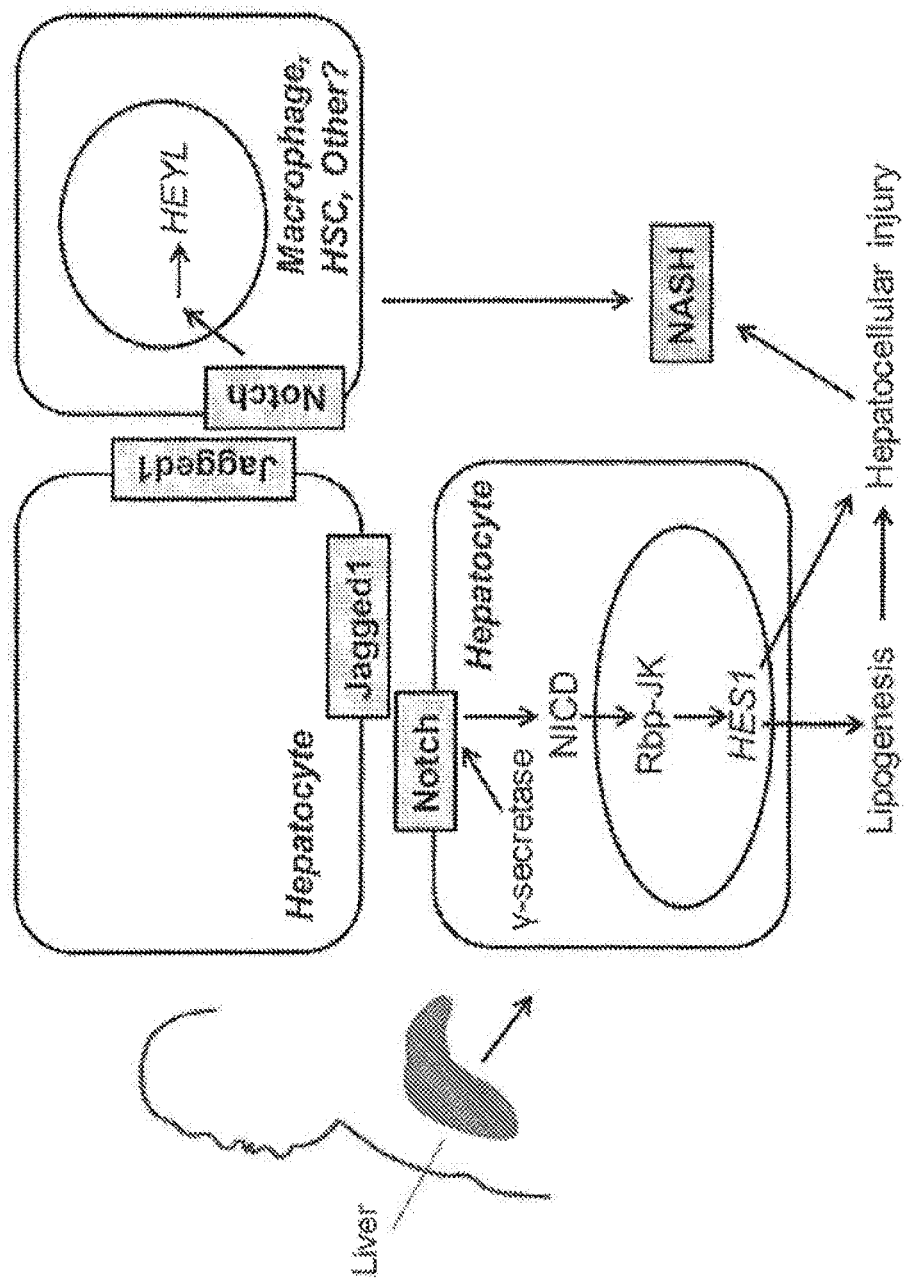
FIG. 2. Proposed model of hepatic Notch signaling.

The present invention provides a method for treating a human subject afflicted with a metabolic disease with a pharmaceutical composition, comprising the steps of:
i) determining JAG1 expression level in the subject;
ii) identifying the subject as a predicted responder if the JAG1 expression level is greater than 1.5 fg/ng 18S; and
iii) administering the pharmaceutical composition to the subject only if the subject is identified as a predicted responder.

The present invention also provides a method of identifying a human subject afflicted with a metabolic disease as a predicted responder or as a predicted non-responder to a pharmaceutical composition, the method comprising determining JAG1 expression in the subject and identifying the human subject as a predicted responder to the pharmaceutical composition if the JAG1 expression level is greater than 1.5 fg/ng 18S, or identifying the human subject as a predicted non-responder to the pharmaceutical composition if the JAG1 expression level is less than 1.0 fg/ng 18S.

The present invention also provides a method of predicting clinical responsiveness to a pharmaceutical composition in a human subject afflicted with metabolic disease, the method comprising evaluating JAG1 expression level in the subject, to thereby predict clinical responsiveness to the pharmaceutical composition.

The present invention also provides a method for treating a human subject afflicted with a metabolic disease with a pharmaceutical composition, comprising the steps of:
i) determining whether the human subject is a responder to the pharmaceutical composition by evaluating JAG1 expression level in the subject; and
ii) administering the pharmaceutical composition to the subject only if the subject is identified as a predicted responder.

In some embodiments, a JAG1 expression level greater than or equal to 1.5 fg/ng 18S is associated with a human subject identified as a predicted responder.

In some embodiments, determining the JAG1 expression in the human subject comprises:
a) obtaining liver cells from the subject;
b) isolating RNA from the liver cells from the subject;
c) subjecting the RNA to reverse transcription, thereby synthesizing cDNA; and
d) subjecting the cDNA to quantitative PCR, to determine the expression level of JAG1 and 18S in the sample.

The present invention also provides a method for diagnosing the human subject afflicted with a metabolic disease as a responder to a pharmaceutical composition comprising:
a) determining the expression level of JAG1 in the subject according to a method of the claimed invention;
b) determining the expression level of JAG1 in a reference subject according to a method of the claimed invention; and
c) diagnosing the human subject afflicted with a metabolic disease as a responder to the pharmaceutical composition if the amount of JAG1 in step (a) is substantially increased compared to the amount JAG1 in step (b).

The present invention also provides a kit for identifying a human subject afflicted with a metabolic disease as a predicted responder or as a predicted non-responder to a pharmaceutical composition, the kit comprising at least one probe specific for JAG1 and at least one probe specific for 18S in the sample.

In some embodiments, the kit of the claimed invention further comprises at least one probe specific for HES1.

In some embodiments, the kit of the claimed invention further comprises at least one probe specific for HEYL.

The present invention also provides a kit for identifying a human subject afflicted with a metabolic disease as a predicted responder or as a predicted non-responder to a pharmaceutical composition, the kit comprising at least one PCR primer designed to amplify a DNA segment specific for JAG1 and at least one at least one PCR primer specific for 18S in the sample.

In some embodiments, the kit of the claimed invention further comprises at least one PCR primer designed to amplify a DNA segment specific for HES1.

In some embodiments, the kit of the claimed invention further comprises at least one PCR primer designed to amplify a DNA segment specific for HEYL.

In some embodiments, the kit of the claimed invention further comprises instructions for use of the kit for identifying a human subject afflicted with a metabolic disease as a predicted responder of as a predicted non-responder to a pharmaceutical composition.

The present invention also provides a method for treating a human subject afflicted with a metabolic disease with a pharmaceutical composition, comprising the steps of:
i) determining JAG1 expression level in the subject;
ii) determining HES1 expression level in the subject;
iii) identifying the subject as a predicted responder if JAG1 expression level is greater than 1.5 fg/ng 18S, and HES1 expression level is greater than 1.5 fg/ng 18S; and
iv) administering the pharmaceutical composition to the subject only if the subject is identified as a predicted responder.

The present invention also provides a method of identifying a human subject afflicted with a metabolic disease as a predicted responder or as a predicted non-responder to a pharmaceutical composition, the method comprising determining JAG1 and HES1 expression levels in the subject and identifying the human subject as a predicted responder to the pharmaceutical composition if the JAG1 expression level is greater than 1.5 fg/ng 18S, and the HES1 expression level is greater than 1.5 fg/ng 18S, or identifying the human subject as a predicted non-responder to the pharmaceutical composition if the JAG1 expression level is less than 1.0 fg/ng 18S and the HES1 expression level is less than 1.5 fg/ng 18S.

The present invention also provides a method of predicting clinical responsiveness to a pharmaceutical composition in a human subject afflicted with metabolic disease, the method comprising evaluating JAG1 and HES1 expression levels in the subject, to thereby predict clinical responsiveness to the pharmaceutical composition.

The present invention also provides a method for treating a human subject afflicted with a metabolic disease with a pharmaceutical composition, comprising the steps of:
  i) determining whether the human subject is a responder to the pharmaceutical composition by evaluating JAG1 and HES1 expression levels in the subject; and
  ii) administering the pharmaceutical composition to the subject only if the subject is identified as a predicted responder.

In some embodiments, a JAG1 expression level greater than or equal to 1.5 fg/ng 18S and a HES1 expression level greater than or equal to 1.0 fg/ng 18S is associated with a human subject identified as a predicted responder.

In some embodiment, determining the JAG1 and HES1 expression levels of the human subject comprises:
  a) obtaining liver cells from the subject;
  b) isolating RNA from the liver cells from the subject;
  c) subjecting the RNA to reverse transcription, thereby synthesizing cDNA; and
  d) subjecting the cDNA to quantitative PCR, to determine the expression level of JAG1, HES1, and 18S in the sample.

The present invention also provides a method for treating a human subject afflicted with a metabolic disease with a pharmaceutical composition, comprising the steps of:
  i) determining JAG1 expression level in the subject;
  ii) determining HES1 expression level in the subject;
  iii) determining HEYL expression level in the subject;
  iv) identifying the subject as a predicted responder if the JAG1 expression level is greater than 1.5 fg/ng 18S, the HES1 expression level is greater than 1.0 fg/ng 18S, and the HEYL expression level is greater than 0.5 fg/ng 18S; and
  v) administering the pharmaceutical composition to the subject only if the subject is identified as a predicted responder.

The present invention also provides a method of identifying a human subject afflicted with a metabolic disease as a predicted responder or as a predicted non-responder to a pharmaceutical composition, the method comprising determining JAG1, HES1, and HEYL expression levels in the subject and identifying the human subject as a predicted responder to the pharmaceutical composition if the JAG1 expression level is greater than 1.5 fg/ng 18S, the HES1 expression level is greater than 1.0 fg/ng 18S, and the HE1Y expression level is greater than 0.5 fg/ng 18S, or identifying the human subject as a predicted non-responder to the pharmaceutical composition if the JAG1 expression level is less than 1.5 fg/ng 18S, the HES1 expression level is less than 1.0 fg/ng 18S, and the HEYL expression level is less than 0.5 fg/ng 18S.

The present invention also provides a method of predicting clinical responsiveness to a pharmaceutical composition in a human subject afflicted with metabolic disease, the method comprising evaluating JAG1, HES1, and HEYL expression levels in the subject, to thereby predict clinical responsiveness to the pharmaceutical composition.

The present invention also provides a method for treating a human subject afflicted with a metabolic disease with a pharmaceutical composition, comprising the steps of:
  i) determining whether the human subject is a responder to the pharmaceutical composition by evaluating JAG1, HES1, and HEYL expression levels in the subject; and
  ii) administering the pharmaceutical composition to the subject only if the subject is identified as a predicted responder.

In some embodiments, a JAG1 expression level greater than or equal to 1.5 fg/ng 18S, a HES1 expression level greater than or equal to 1.0 fg/ng 18S, and HEYL expression level is greater than 0.5 fg/ng 18S is associated with a human subject identified as a predicted responder.

In some embodiment, determining the JAG1, HES1, and HEYL expression levels of the human subject comprises:
  a) obtaining liver cells from the subject;
  b) isolating RNA from the liver cells from the subject;
  c) subjecting the RNA to reverse transcription, thereby synthesizing cDNA; and
  d) subjecting the cDNA to quantitative PCR, to determine the expression level of JAG1, HES1, HEYL, and 18S in the sample.

In some embodiments, the pharmaceutical composition is an agent for the treatment of fatty liver disease.

In some embodiments, the pharmaceutical composition is vitamin E, selenium, betadine, metformin, rosiglitazone, piogliatazone, insulin sensitizers, antioxidants, probiotics, Omega-3 DHA, pentoxifylline, anti-TNF-alpha, FXR agonists, and GLP-1 agonist.

In some embodiments, the pharmaceutical composition is vitamin E, piogliatazone, or obeticholic acid.

In some embodiments, the pharmaceutical composition is a Notch inhibitor.

In some embodiments, the pharmaceutical composition decreases JAG1 expression level.

In some embodiments, the pharmaceutical composition inhibits interaction of Jagged1 and Notch.

In some embodiments, the compound reduces the expression level of HES1 or HEYL.

In some embodiments, the pharmaceutical composition comprises a polynucleotide.

In some embodiments, the pharmaceutical composition is targeted to the liver of the subject.

In some embodiments, the metabolic disease is obesity.

In some embodiments, the metabolic disease is hypertriglyceridemia.

In some embodiments, the metabolic disease is hyperinsulinemia.

In some embodiments, the metabolic disease is Type 2 Diabetes.

In some embodiments, the metabolic disease is fatty liver disease.

In some embodiments, the fatty liver disease is nonalcoholic fatty liver disease.

In some embodiments, the fatty liver disease is nonalcoholic steatohepatitis.

In some embodiments, the subject is afflicted with cirrhosis or hepatocellular carcinoma.

In some embodiments, identifying the subject as a predicted responder if the JAG1 expression level is greater than 1.0, 1.1, 1.2, 1.3, 1.4, 1.5, 1.6, 1.7, 1.8, 1.9, or 2.0 fg/ng 18S.

In some embodiments, identifying the subject as a predicted responder if the HES1 expression level is greater than 0.5, 0.6, 0.7, 0.8, 0.9, 1.0, 1.1, 1.2, 1.3, 1.4, or 1.5 fg/ng 18S.

In some embodiments, identifying the subject as a predicted responder if the HEYL expression level is greater than 0.2, 0.3, 0.4, 0.5, 0.6, 0.7, 0.8, 0.9, or 1.0 fg/ng 18S.

In some embodiments, identifying the subject as a predicted nonresponder if the JAG1 expression level is less than 0.5, 0.6, 0.7, 0.8, 0.9, 1.0, 1.1, 1.2, 1.3, 1.4, or 1.5 fg/ng 18S.

In some embodiments, identifying the subject as a predicted nonresponder if the HES1 expression level is less than 0.2, 0.3, 0.4, 0.5, 0.6, 0.7, 0.8, 0.9, or 1.0 fg/ng 18S.

In some embodiments, identifying the subject as a predicted nonresponder if the HEYL expression level is less than 0.2, 0.3, 0.4, or 0.5 fg/ng 18S.

In some embodiments, identifying the subject as a predicted responder if the JAG1 expression level is substantially increased compared to the JAG1 expression level in a reference subject.

In some embodiments, identifying the subject as a predicted responder if the HES1 expression level is substantially increased compared to the HES1 expression level in a reference subject.

In some embodiments, identifying the subject as a predicted responder if the HEYL expression level is substantially increased compared to the HEYL expression level in a reference subject.

In some embodiments, identifying the subject as a predicted nonresponder if the JAG1 expression level is substantially the same as compared to the JAG1 expression level in a reference subject.

In some embodiments, identifying the subject as a predicted nonresponder if the HES1 expression level is substantially the same as compared to the HES1 expression level in a reference subject.

In some embodiments, identifying the subject as a predicted non-responder if the HEYL expression level is substantially the same as compared to the HEYL expression level in a reference subject.

In some embodiments, identifying the subject as a predicted responder prior to administering the pharmaceutical composition.

In some embodiments, determining the JAG1, HES1, or HEYL expression level is prior to administering the pharmaceutical composition.

In some embodiments, determining the JAG1, HES1, or HEYL expression level is after administering the pharmaceutical composition.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

This invention will be better understood by reference to the Experimental Details which follow, but those skilled in the art will readily appreciate that the specific experiments detailed are only illustrative of the invention as described more fully in the claims which follow thereafter.

Terms

As used herein, "about" in the context of a numerical value or range means±10% of the numerical value or range recited or claimed, unless the context requires a more limited range.

As used herein, "a subject afflicted with" a disease, e.g. nonalcoholic fatty liver disease, means a human patient who was been affirmatively diagnosed to have the disease.

As used herein, "effective" when referring to an amount of a compound or compounds refers to the quantity of the compound or compounds that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the physical condition of the patient, the type of subject being treated, the duration of the treatment, the nature of concurrent therapy (if any), and the specific formulations employed and the structure of the compounds or its derivatives.

In some embodiments, "a subject in need" includes a subject with elevated triglyceride levels, e.g., a subject with plasma or serum triglyceride level greater than 150 mg/dL, greater than 200 mg/dL, or to greater than 500 mg/dL.

In some embodiments, a subject afflicted with a metabolic disease, such as obesity, tends to have elevated triglyceride levels.

In some embodiments, a pharmaceutical composition comprises a pharmaceutical carrier and a compound.

In some embodiments, the pharmaceutical composition is manufactured, wherein the pharmaceutical composition comprises an isolated or purified naturally occurring compound.

In some embodiments, the pharmaceutical composition is manufactured, wherein the pharmaceutical composition comprises a compound which was not produced by a process in nature.

In some embodiments, a reference subject includes a subject with plasma or serum triglyceride level less than 150 mg/dL.

In some embodiments, a reference subject includes a subject not afflicted with a metabolic disease.

"Notch", "Notch protein", and "Notch receptor protein" are synonymous. In addition, the terms "Notch-based fusion protein" and "Notch decoy" are synonymous. The following Notch amino acid sequences are known and hereby incorporated by reference: Notch1 (Genbank accession no. S18188 (rat)); Notch2 (Genbank accession no. NP_077334 (rat)); Notch3 (Genbank accession no. Q61982 (mouse)); and Notch4 (Genbank accession no. T09059 (mouse)). The following Notch nucleic acid sequences are known and hereby incorporated by reference: Notch1 (Genbank accession no. XM_342392 (rat) and NM_017617 (human)); Notch2 (Genbank accession no. NM_024358 (rat), M99437 (human and AF308601 (human)); Notch3 (Genbank accession no. NM_008716 (mouse) and XM_009303 (human)); and Notch4 (Genbank accession no. NM_010929 (mouse) and NM_004557 (human)).

"Notch decoy protein", as used herein, means a fusion protein comprising a portion of a Notch receptor protein which lacks intracellular signaling components and acts as a Notch signaling antagonist. Notch decoy proteins comprise all or a portion of a Notch extracellular domain including all or a portion of the EGF-like repeats present in the Notch extracellular domain. Examples of Notch decoy proteins include fusion proteins which comprise (a) amino acids, the sequence of which is identical to the sequence of a portion of the extracellular domain of a human Notch receptor protein and (b) amino acids, the sequence of which is identical to the sequence of an Fc portion of an antibody. In some Notch decoy proteins (b) is located to the carboxy terminal side of (a). Some Notch decoy proteins further comprise a linker sequence between (a) and (b). Notch decoy proteins can be selected from the group consisting of human Notch1 receptor protein, human Notch2 receptor protein, human Notch3 receptor protein and human Notch4 receptor protein. In some Notch decoy proteins the extracellular domain of the human Notch receptor protein is selected from the group consisting of Notch1 EGF-like repeats 1-36, Notch1 EGF-like repeats 1-13, Notch1 EGF-like repeats 1-24, Notch1 EGF-like repeats 9-23, Notch1 EGF-like repeats 10-24, Notch1 EGF-like repeats 9-36, Notch1 EGF-like repeats 10-36, Notch1 EGF-like repeats 14-36, Notch1 EGF-like repeats 13-24, Notch1 EGF-like repeats 14-24, Notch1 EGF-like repeats 25-36, Notch4 EGF-like repeats 1-29, Notch4 EGF-like repeats 1-13, Notch4 EGF-like repeats 1-23, Notch4 EGF-like repeats 9-23, Notch4 EGF-like repeats 9-29, Notch4 EGF-like repeats 13-23, and Notch4 EGF-like repeats 21-29.

Examples of Notch decoy proteins can be found in U.S. Pat. No. 7,662,919 B2, issued Feb. 16, 2010, U.S. Patent Application Publication No. US 2010-0273990 A1, U.S. Patent Application Publication No. US 2011-0008342 A1, U.S. Patent Application Publication No. US 2011-0223183 A1 AND PCT International Application No. PCT/US2012/058662; the entire contents of each of which are hereby incorporated by reference into this application.

As used herein, a treatment of fatty liver disease may include any agent, pharmaceutical composition, therapy known to or thought to treat a fatty liver disease. Treatment of obesity include, but are not limited to vitamin E, selenium, betaine, metformin, rosiglitazone, pioglitazone, insulin sensitizers, antioxidants, probiotics, Omega-3 DHA, pentoxifylline, anti-TNF-alpha, FXR agonists and GLP-1 agonists.

Antisense Oligonucleotide

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of target gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of gene expression can be obtained by designing antisense oligonucleotides which will form duplexes to the control, 5', or regulatory regions of the gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (Nicholls et al., 1993, J Immunol Meth 165:81-91). An antisense oligonucleotide also can be designed to block translation of mRNA by preventing the transcript from binding to ribosomes.

Precise complementarity is not required for successful complex formation between an antisense oligonucleotide and the complementary sequence of a target polynucleotide. Antisense oligonucleotides which comprise, for example, 1, 2, 3, 4, or 5 or more stretches of contiguous nucleotides which are precisely complementary to a target polynucleotide, each separated by a stretch of contiguous nucleotides which are not complementary to adjacent nucleotides, can provide sufficient targeting specificity for a target mRNA. Preferably, each stretch of complementary contiguous nucleotides is at least 4, 5, 6, 7, 8, 9, 10, 11, 12, 13, 14, 15, 16, 17, 18, 19, 20, 21, 22, 23, 24, 25, or more nucleotides in length. Noncomplementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular target polynucleotide sequence. Antisense oligonucleotides can be modified without affecting their ability to hybridize to a target polynucleotide. These modifications can be Internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art.

Adenoviral Vector

An adenoviral vector encodes an oligonucleotide. The use of adenoviral vectors in gene therapy and tissue-specific targeting has been described in Beatty and Curiel, 2012, Barnett et al., 2002, and Rots et al., 2003, the contents of which are incorporated herein by reference.

Methods of Administration

"Administering" compounds in embodiments of the invention can be effected or performed using any of the various methods and delivery systems known to those skilled in the art. The administering can be, for example, intravenous, oral, intramuscular, intravascular, intra-arterial, intracoronary, intramyocardial, intraperitoneal, and subcutaneous. Other non-limiting examples include topical administration, or coating of a device to be placed within the subject.

Injectable Drug Delivery

Injectable drug delivery systems may be employed in the methods described herein include solutions, suspensions, gels.

Oral Drug Delivery

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc). Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

For oral administration in liquid dosage form, a PHLPP2 or Raptor activator may be combined with any oral, non-toxic, pharmaceutically acceptable inert carrier such as ethanol, glycerol, water, and the like.

Pharmaceutically Acceptable Carrier

The compounds used in embodiments of the present invention can be administered in a pharmaceutically acceptable carrier. As used herein, a "pharmaceutically acceptable carrier" is a pharmaceutically acceptable solvent, suspending agent or vehicle, for delivering the compounds to the subject. The carrier may be liquid or solid and is selected with the planned manner of administration in mind. Liposomes such as small unilamellar vesicles, large unilamallar vesicles, and multilamellar vesicles are also a pharmaceutically acceptable carrier. Liposomes can be formed from a variety of phospholipids, such as cholesterol, stearylamine, or phosphatidylcholines. The compounds may be administered as components of tissue-targeted emulsions. Examples of lipid carriers for antisense delivery are disclosed in U.S. Pat. Nos. 5,855,911 and 5,417,978, which are incorporated herein by reference. The compounds used in the methods of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

A compound of the invention can be administered in a mixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297, issued Sep. 2, 1975.

Tablets

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Specific Administration to Liver

Embodiments of the invention relate to specific administration to the liver or hepatocytes.

In some embodiments, a compound may specifically target the liver.

In some embodiments, a compound may specifically target hepatocytes.

In some embodiments, a compound may be specifically targeted to the liver by coupling the compound to ligand molecules, targeting the compound to a receptor on a hepatic cell, or administering the compound by a bio-nanocapsule.

A compound of the invention can also be administered by coupling of ligand molecules, such as coupling or targeting moieties on preformed nanocarriers, such as (PGA-PLA nanoparticles, PLGA nanoparticles, cyclic RGD-doxorubicin-nanoparticles, and poly(ethylene glycol)-coated biodegradable nanoparticles), by the post-insertion method, by the Avidin-Biotin complex, or before nanocarriers formulation, or by targeting receptors present on various hepatic cell, such as Asialoglycoproein receptor (ASGP-R), HDL-R, LDL-R, IgA-R, Scavenger R, Transferrin R, and Insulin R, as described in: Mishra et al., (2013) Efficient Hepatic Delivery of Drugs: Novel Strategies and Their Significance, BioMed Research International 2013: 382184, dx.doi.org/10.1155/2013/382184, the entire contents of which are incorporated herein by reference.

A compound of the invention can also be administered by bio-nanocapsule, as described in: Yu et al., (2005) The Specific delivery of proteins to human liver cells by engineered bio-nanocapsules, FEBS Journal 272: 3651-3660, dx.doi.org/10.1111/j.1742-4658.2005.04790.x, the entire contents of which are incorporated herein by reference.

In some embodiments, an oligonucleotide specifically targets the liver.

In some embodiments, an oligonucleotide specifically targets hepatocytes.

Antisense oligonucleotides of the invention can also be targeted to hepatocytes, as described in: Prakash et al., (2014) Targeted delivery of antisense oligonucleotides to hepatocytes using triantennary N-acetyl galactosamine improves potency 10-fold in mice, Nucleic Acids Research 42(13): 8796-8807, dx.doi.org/10.1093/nar/gku531, the entire contents of which are incorporated herein by reference.

As used herein, the term "effective amount" refers to the quantity of a component that is sufficient to treat a subject without undue adverse side effects (such as toxicity, irritation, or allergic response) commensurate with a reasonable benefit/risk ratio when used in the manner of this invention, i.e. a therapeutically effective amount. The specific effective amount will vary with such factors as the particular condition being treated, the physical condition of the patient, the type of subject being treated, the duration of the treatment, the nature of concurrent therapy (if any), and the specific formulations employed and the structure of the compounds or its derivatives.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

The dosage of a compound of the invention administered in treatment will vary depending upon factors such as the pharmacodynamic characteristics of the compound and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds of the invention may comprise a compound alone, or mixtures of a compound with additional compounds used to treat cancer. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection or other methods, into the eye, all using dosage forms well known to those of ordinary skill in the pharmaceutical arts.

In an embodiment, the pharmaceutical composition may be administered once a day, twice a day, every other day, once weekly, or twice weekly. A subject's triglyceride level may be expressed herein as plasma triglyceride or serum triglyceride.

Where a range is given in the specification it is understood that the range includes all integers and 0.1 units within that range, and any sub-range thereof. For example, a range of 1 to 5 is a disclosure of 1.0, 1.1, 1.2, etc.

This invention will be better understood by reference to the Examples which follow, but those skilled in the art will readily appreciate that the specific experiments detailed are only illustrative of the invention as described more fully in the claims which follow thereafter.

Example 1

Notch Activity is a Therapeutically-Accessible Pathway Activated in Obese Liver.

Notch is an evolutionarily conserved regulatory pathway of normal development (Bolos 2007). Initial characterization in murine liver demonstrated that the Notch pathway was active in healthy, adult mice and physiologically modulated by nutrient availability, but markedly increased in mouse models of obesity and insulin resistance. It was hypothesized that increased Notch activity is causative of, and not just correlated to, obesity-induced T2D and NAFLD. As there are 4 Notch receptors, mice were generated lacking the specific transcription factor downstream of all Notch signaling, Rbp-Jk (Oka 1995), in postnatal hepatocytes (L-Rbpj mice). In parallel, to exclude the possibilities of either Notch-independent Rbp-Jk signaling or Rbp-Jk-independent Notch effects, an alternative Notch loss-of-function mouse model was generated by genetically ablating Nicastrin, the targeting subunit of the gamma-secretase complex necessary for Notch activity (L-Ncst mice) (De Strooper 2005). Despite comparable body weight and adiposity (FIG. 1a), HFD-fed L-Rbpj and L-Ncst mice showed improved glucose tolerance (FIG. 1b), and less liver triglyceride (TG) (FIG. 1c) than Cre-controls, proving that Notch contributes to T2D and NAFLD risk. These loss-of-function studies suggested that Notch signaling is permissive for maximal obesity-induced metabolic dysfunction. It was hypothesized that Notch gain-of-function would be sufficient to induce glucose intolerance and fatty liver in vivo. To test this, wildtype (WT), chow-fed mice were transduced with adenovirus encoding constitutively active Notch1 (N1-IC). A low titer of virus was selected to mimic the 2-3 fold endogenous induction of hepatic Notch activity in HFD-fed or ob/ob mice (Pajvani 2011). As hypothesized, N1-IC transduced mice developed fatty liver and glucose intolerance (FIGS. 1d-f).

It was predicted that pharmacologic blockade of liver Notch signaling could recapitulate the phenotype of L-Rbpj and L-Ncst mice—indeed, treatment of obese mice with specific Notch inhibitors termed "Decoys" (Dufraine 2008;

Funashi 2008; Funashi 2011) resulted in parallel inhibition of both hepatic glucose production and TG accumulation (Pajvani 2001; Pajvani 2013). These data were confirmed by work at other laboratories using different Notch inhibitors (Fukada 2012; Li 2013), suggesting that inhibition of Notch represents a novel means of reducing metabolic disease burden as obesity rates continue to rise. Data suggested that monoclonal antibodies to Notch receptors or the Jagged family of Notch ligands show good efficacy and safety profiles (Espinoza 2013), whereas those that target Delta-like ligands may paradoxically induce hemangiomas (Yan 2011), underscoring the rationale for understanding how Notch is activated in obese liver to determine whether these drugs can be repurposed for T2D, where the ratio of benefit/acceptable risk is markedly different than for cancer, or for NASH, an "orphan" disease (Gawrieh 2015) lacking approved pharmacotherapy (Ratziu 2015).

Example 2

Notch is Active in NASH.

A similar survey was conducted in humans. In a cross-sectional study in patients with suspected NASH undergoing liver biopsy, it was found that Notch signaling was positively correlated with insulin resistance, as well as hepatic triglyceride content, but showed independent and greatest correlation with plasma aminotransferase (ALT) levels and NAFLD activity score (NAS), biochemical and pathologic markers of the hepatocellular dysfunction, inflammation and fibrosis that defines NASH (Valenti 2013). Notch activity was shown to track with NASH outcomes. In combination with mouse studies, these data suggested that Notch may represent a therapeutically accessible mediator of the multiple hit model of NASH development (Yilmaz 2012).

Notch signaling is critical for cell fate decision-making in normal development (Bolos 2007), but less is known about the homeostatic effects of Notch in developed tissue. In liver, Notch proteins were found to be constitutively expressed in multiple liver cell types (Nijjar 2001; Nijjar 2002), with increased expression in hepatocytes following partial hepatectomy (Kohler 2004), Further, liver regenerative capacity was found to be altered by inhibition of hepatocyte Notch signaling (Wang 2009). As such, it was predicted that Notch activity may increase in response to obesity-induced hepatocyte damage, and may be causative to the inflammatory and fibrotic state that characterizes NASH. This concept was in agreement with previous studies showing that hepatic Notch activity was regulated by pathophysiologic (fasting/refeeding, insulin resistance, nutrient excess) metabolic cues (Pajvani 2011; Pajvani 2013), and that Notch activity may be genetically or pharmacologically manipulated to reduce obesity-related glucose intolerance, hepatic steatosis and even steatohepatitis.

A model of hepatic Notch signaling is shown in FIG. 2.

Example 3

Hepatic Notch Signaling

Example 3A

Hepatocyte Notch activation induces fatty liver and exacerbates steatohepatitis in mice, consistent with the ideally positioned role of Notch to mediate cellular cross-talk. Hepatocyte Notch activation is a key mechanism in the pathogenesis of NASH.

Example 3B

Liver Notch signaling tracks with NASH activity, increased in patients with higher NAS scores and decreased by NASH pharmacotherapy.

Different Notch target genes representing Notch-active hepatocytes (HES1) and non-hepatocytes (HEYL) effectively show causation in animal studies and correlation with NASH activity in patients, and represent activation in different liver cellular compartments.

Example 3C

Expression of the Notch ligand JAG1 predicts the natural history of NAFLD/NASH, including the therapeutic efficacy of NASH pharmacotherapy, and represents the first diagnostic to have predictive value—a potentially transformative finding in the clinical management of NASH.

Example 4

Hepatic Notch Activity was Increased in Mouse "NASH"

Most metabolism studies are performed in high-fat diet (HFD)-fed animals, to induce obesity and consequent insulin resistance. HFD-feeding also induces marked hepatic steatosis, with lipid content approaching 20% on a gram per gram basis, but this does not translate to the hepatocyte injury seen in human NASH, or the fibrotic reaction seen in human cirrhosis. In the past, the most frequently used model for mouse "NASH" was methionine and choline deficient diets (MCDD) (Rinella 2004). MCDD-fed mice develop macrovesicular steatosis, lobular inflammation and fibrosis (Kohli 2011), but unlike human NASH, MCDD-fed animals tend to lose weight and, as such, are more insulin-sensitive than control animals (Rinella 2008). This discordance from human NASH has led many investigators to utilize a high-fat, high-carbohydrate diet supplemented with high-fructose corn syrup-equivalent drinking water (henceforth, HFHC diet) (Kohli 2011; Kohli 2010). HFHC-feeding induces obesity, and similar insulin resistance and hepatic steatosis as HFD-fed animals (Kohli 2010).

Unlike HFD-feeding, however, HFHC-feeding induces: 1) Hepatocellular injury, as assessed by hepatocyte apoptosis (TUNEL staining), and plasma ALT levels; 2) Liver inflammation, as measured by immunohistochemical (F4/80 staining) and qPCR evaluation for macrophage infiltration (Emr1, Cd68) and activity (Mcp1, Tnfa); and 3) Fibrosis, marked by HSC activation, leading to increased collagen expression (Colla1, and others) and Masson's trichrome staining (Ibrahim 2013).

Thus, HFHC-feeding reproduces all three key aspects of human NASH (hepatocyte injury, inflammation and fibrosis), and as such, is the current state of the art in terms of mouse modeling of this complex condition. Indeed, as reported (Kohli 2010), it was found that wildtype mice allowed ad libitum access to HFHC diet for 16 weeks become obese, insulin-resistant and, importantly, show evidence of steatohepatitis and fibrosis (FIGS. 4a-c). In parallel, HFHC-feeding significantly increased hepatic Hes1 and HeyL expression (FIG. 4d), which showed remarkable correlation to plasma ALT levels (FIG. 4.), suggesting that Notch activity in murine liver is associated with "NASH". Next, hepatocytes and non-hepatocytes were isolated from chow- or HFHC-fed mice by differential centrifugation, and consistent with our examinations, it was found higher hepatocyte Hes1 expression and non-hepatocyte HeyL in mice with steatohepatitis (FIG. 4f).

Example 5

Notch Exacerbates HFHC-Induced Steatohepatitis and Fibrosis

To test if Notch was causative to HFHC-induced liver injury, Cre- and hepatocyte-specific Notch gain-of-function (SA-ERT2-Cre$^{51}$:NICD$^{fl/fl\ 52}$ mice, henceforth L-NICD) mice (Chen 2001) were exposed to HFHC diet prior to inducing recombination of this constitutively-active form of Notch with tamoxifen. L-NICD mice showed elevated plasma ALT levels, as well as evidence of increased inflammatory cell and HSC activity (FIGS. 5a, b). Conversely, hepatocyte-specific Notch loss-of-function (L-Ncst or L-Rbpj mice), showed the opposite phenotype (Figure Sc), proving the necessity of intact hepatocyte Notch signaling in the full development of steatohepatitis/fibrosis.

Example 6

Hepatic Notch Activity is Associated with Steatohepatitis, Independent of Insulin Resistance and More Strongly than Hepatic Lipid Content Whether these intriguing mouse data translated to patients with T2D and NAFLD/NASH was not known. A small, cross-sectional study was performed in patients undergoing outpatient liver biopsy in evaluation for abnormal liver function tests (Valenti 2013). In this study, it was found that hepatic Notch activity (as assessed by HES1 and HEYL expression) was positively correlated with insulin resistance, as well as hepatic triglyceride content, but showed greatest correlation with plasma aminotransferase (ALT) levels and NAFLD activity score (NAS), markers of the progression from NAFLD to NASH (FIGS. 6a, b). As such, patients with NAS>2, correlating with high risk of NASH (Kleiner 2005; Sanyal 2011), have increased HES1/HEYL expression (FIG. 6c), with synergistic increase in patients with NASH and insulin-resistance (FIG. 6d).

Example 7

Notch Activity is Reduced in Patients Who Responded to Therapy in the PIVENS Trial A pilot Ancillary Study to the Pioglitazone versus Vitamin E versus Placebo for the Treatment of nondiabetic Patients with Nonalcoholic Steatohepatitis (PIVENS) trial (Sanyal 2010), was conducted to ask whether hepatic Notch signaling tracks with disease pathology, and thus represent a novel biomarker of NAFLD/NASH.

PIVENS investigators randomized adult, non-diabetic patients with NASH to therapy with placebo, vitamin E (800 IU daily) or pioglitazone (30 mg daily), and had strict inclusion and exclusion criteria for trial entry, as well as a thorough clinical phenotyping of these patients (Sanyal 2011; Sanyal 2010). The PIVENS primary outcome was an improvement in NASH pathology, defined by improved hepatocellular ballooning without increase in fibrosis, and either a 2+ point decrease in NAS or to a score of ≤3 points. In the final analysis, vitamin E-treated patients met the primary outcome, whereas pioglitazone treatment was a near-miss, showing a trend towards benefit in the primary outcome and equal or greater efficacy as vitamin E at hitting the NASH secondary outcomes (ALT levels, total NAS score as well as its component steatosis, hepatocellular ballooning and lobular inflammation scores).

Example 8

Role of Notch Signaling as a Biomarker or Contributor to the NAFLD/NASH Pathology Research-grade specimens were saved from subjects from the PIVENS trial for Ancillary Studies (Chalsani 2009). These samples were used to test the potential role of Notch signaling as either a biomarker or contributor to the NAFLD/NASH pathology. Analyses from PIVENS is shown in Table 1.

TABLE 1

Analysis of PIVENS trial

| | Cross-sectional study (n = 118; 46 M/72 F) | | | Longitudinal study (n = 21; 11 M/10 F) | | |
|---|---|---|---|---|---|---|
| | Placebo | VitE | PIO | Placebo | VitE | PIO |
| Number | 40 | 41 | 37 | 7 | 10 | 4 |
| Age, years | 45 ± 2 | 49 ± 2 | 49 ± 2 | 51 ± 4 | 40 ± 4 | 44 ± 8 |
| BMI, kg/m$^2$ | 36 ± 1 | 35 ± 1 | 35 ± 1 | 35 ± 3 | 37 ± 3 | 35 ± 4 |
| Responders (%) | 15 (38%) | 25 (61%) | 29 (78%) | 2 (29%) | 6 (60%) | 3 (75%) |

| | NR | R | NR | R | NR | R | NR | R | NR | R | NR | R |
|---|---|---|---|---|---|---|---|---|---|---|---|---|
| NAS ± SEM | 4.9 ± 0.3 | 2.9# ± 0.3 | 4.6 ± 0.3 | 2.7# ± 0.2 | 4.8 ± 0.5 | 2.2# ± 0.2 | 5.8 ± 0.4 | 3.0 ± 0.1 | 3.9 ± 0.4 | 2.6 ± 0.2 | 5.0 ± xx | 3.0 ± 0.3 |
| ALT (U/L) ± SEM | 67 ± 5 | 48* ± 8 | 55 ± 9 | 33 ± 4 | 46 ± 7 | 34* ± 3 | 71 ± 9 | 40 ± 7 | 58 ± 14 | 45 ± 12 | 56 ± xx | 41 ± 12 |
| HOMA-IR ± SEM | 5.0 ± 0.5 | 3.8 ± 0.5 | 5.6 ± 0.6 | 5.2 ± 0.6 | 5.5 ± 0.8 | 2.9* ± 0.5 | 4.8 ± 1.9 | 2.9 ± 1.9 | 5.1 ± 0.5 | 5.1 ± 1.3 | 4.1 ± xx | 3.3 ± 1.3 |

*P < 0.05;
P < 0.001
xx unable to be calculated
NAS, NAFLD Activity Score
NR, Nonresponders;
R, Responders 1) Cross-Sectional Study:

"Responders", defined as research subjects who either demonstrated NASH resolution or met the primary PIVENS outcome, had lower NAS and ALT as compared to "non-responders" (Table 1, left), and a parallel reduction in HES1 and HEYL expression in end-of-treatment (96 wk) liver biopsies (FIG. 7a). To explain lower HES1/HEYL expression, Notch signaling components were surveyed and found, surprisingly, that the only Notch receptor or ligand to significantly differ between responders and non-responders is JAG1 (FIGS. 7b, c). Combined with data showing correlation with lower NAS score and plasma ALT levels (Valenti 2013), these results effectively demonstrate that hepatic Notch signaling, driven by JAG1, is a biomarker of NASH activity.

Figure 8A:
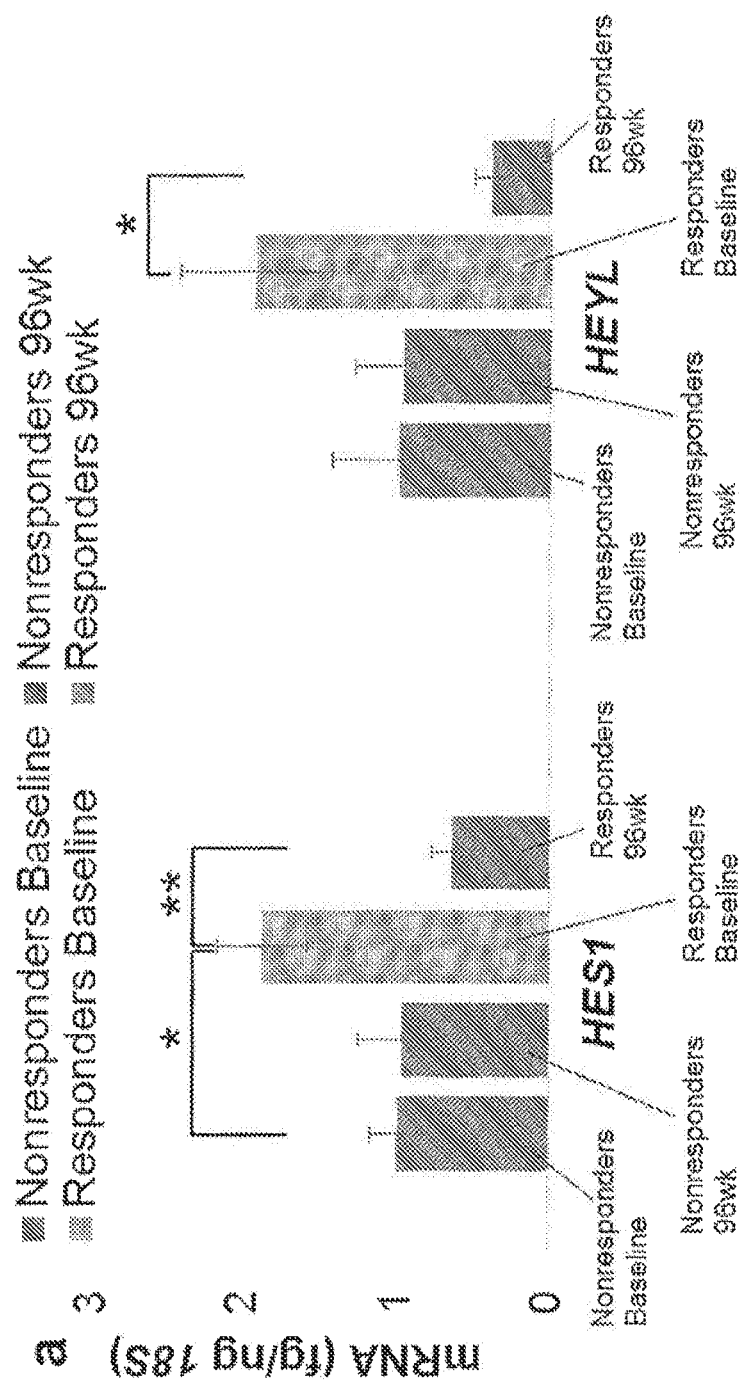

2) Longitudinal Study:

A subset (Table 1, right), of PIVENS research subjects had paired baseline and 96 wk cDNA available for analysis. These cDNA pairs were examined for changes in hepatic Notch activity, and both HES1 and HEYL expression were found to be significantly reduced in PIVENS responders, but unchanged in non-responders (FIG. 8a). Unexpectedly, this was found to be due primarily to higher baseline HES1 and HEYL in responders than non-responders (FIG. 8a). Based on these results, Notch receptor and ligand expression were surveyed in this cohort, and a striking 7-fold increased JAG1 expression was found in patients who were destined to respond to PIVENS therapy (FIG. 8b), without change in other Notch receptors or ligands. To test whether JAG1 was associated with treatment-induced change in NASH pathology at the individual patient level, change in JAG1 expression was calculated from baseline to 96 wk visits ($\Delta$JAG1), and $\Delta$JAG1 was found to be correlated with change in HES1/HEYL expression, and more impressively, these results explained >37% of the variance in NAS score and plasma ALT levels in these patients (FIG. 8c).

Combined, these data effectively demonstate that high baseline JAG1-driven Notch activity "predicts" either the therapeutic responsiveness or natural history of NASH. In fact, when a post-hoc cutoff was assigned of >1.5 fg JAG1/ng 18S, hereafter referred to as JAG1-high patients, a positive predictive value (PPV) 100% and negative predictive value (NPV) 78.6% was calculated for therapeutic response in PIVENS.

Example 9

Notch is a Biomarker of NASH Activity

Farnesoid X nuclear receptor ligand obeticholic acid for non-cirrhotic, non-alcoholic steatohepatitis (FLINT) was a multicenter, randomized trial of 72 wk treatment with the synthetic bile acid/FXR agonist obeticholic acid (OCA) or placebo in adult patients with biopsy-confirmed NASH (Neuschwander-Tetri 2015). As in PIVENS, patients with cirrhosis, as well as those with suspected other causes of liver disease were excluded from the trial. The primary outcome of FLINT was improvement in NAS by at least 2 points without worsening of fibrosis; multiple secondary histological, biochemical and anthropometric outcomes were also defined. FLINT was stopped early by the Data and Safety Monitoring Board (DSMB) due to demonstrated superiority of OCA at interim analysis, with 43% of OCA-treated patients meeting the primary outcome as compared to 21% of placebo-treated patients. Specifically, OCA treatment showed comparable placebo-adjusted reductions in Nonalcoholic Steatohepatitis Activity Score (NAS) (−0.9, p<0.0001) and alanine aminotransferase (ALT) levels (−20 U/L, p<0.0001) to pioglitazone-treated patients in the PIVENS trial. Unlike pioglitazone treatment, however, OCA increased insulin resistance (reflected in +29 pmol/L insulin, p=0.02; and +13 U HOMA-IR, p=0.01), consistent with OCA-induced exacerbation of the pro-atherogenic lipid profile found in these obese patients, with significant lowering of the cardioprotective HDL cholesterol.

Example 9A—Cross-Sectional Analysis of Responders in the FLINT Trial Show Reduced HES1 and HEYL In Farnesoid X nuclear receptor ligand obeticholic acid for non-cirrhotic, non-alcoholic steatohepatitis (FLINT), obeticholic acid (OCA) clearly induced insulin resistance. Using samples from the FLINT trial, RNA is extracted from liver biopsy specimens preserved in RNAlater® (Thermo Fisher Scientific) from all 200 patients studied in FLINT who had 72 wk end-of-treatment biopsies (n=102 placebo, n=98 OCA). Next, using quantitative PCR, gene expression is assayed of known FXR targets (including SHP, OSTA/B and PPARA (Teodoro 2011)) as a positive control for OCA-treatment, and then Notch target genes (HES1/HEYL) (Valenti 2013) are assayed.

Preliminary data from PIVENS demonstrated 38% lower HES1 (1.06 fg/ng 18S vs. 1.71 fg/ng 18S) and 60% lower HEYL (0.54 fg/ng 18S vs. 1.36 fg/ng 18S) expression in end-of-treatment biopsies from responders as compared to non-responders. If pioglitazone-treated patients are excluded these effect sizes were only modestly attenuated— 36% reduced HES1 (1.08 fg/ng 18S) and 49% reduced HEYL (0.71 fg/ng 18S). To be conservative, we used these latter results to extrapolate to OCA-treated patients, who achieved a similar NAS reduction as compared to Vitamin E-treated patients in PIVENS. With these data, we calculated using unpaired t-testing with type I error=0.05 and type II error=0.8 that we would need 36 and 20 subjects in each group to detect statistically lower HES1 and HEYL expression, respectively, in patients who achieved the primary outcome in FLINT.

Sufficient power to detect a significant difference is demonstrated. OCA treatment is associated with reduced HES1 and HEYL expression. HES1 and HEYL expression are lower in FLINT responders than non-responders.

Example 9B—Longitudinal Analysis of Responders in the FLINT Trial Show Reduced Liver HES1 and HEYL and that $\Delta$HES1 and $\Delta$HEYL Levels Will Positively Correlate with Change in NAS and ALT Paired baseline and 72 wk cDNA derived from FLINT biopsies are analyzed by qPCR for FXR target and HES1/HEYL expression as described in Example 9A. Change in HES1/HEYL gene expression over the trial length is correlated to key clinical outcomes obtained from the NASH CRN Data Coordination Center ($\Delta$NAS and $\Delta$ALT levels) by scatter plot, with correlation coefficient and significance determined by Pearson.

Sample size calculations are based from PIVENS data as described in Example 9A, and exclude pioglitazone-treated patients to be conservative. Using data derived from paired samples in Vitamin E-treated responders (mean difference of 1.11±0.51 fg/ng 18S for HES1 and 2.27±0.71 fg/ng 18S for HEYL), we calculated using unpaired t-testing with type I error=0.05 and type II error=0.8, that 12 before-and-after biopsies in FLINT are required to detect a statistically significant difference in OCA-responders for both HES1 and HEYL.

In OCA-treated responders, liver HES1 and HEYL are lower at end-of-treatment as compared to baseline, and correlate with change in NASH activity. In OCA-treated non-responders, liver HES1 and HEYL increased or unchanged at end-of-treatment as compared to baseline. ΔHES1 and ΔHEYL levels are positively correlate with change in NAS and ALT.

Therefore, hepatic Notch signaling is a NASH biomarker independent of altered hepatic insulin sensitivity.

Example 10

Signaling Cell/Ligand for Liver Notch Signaling

Liver Notch activity reflects contributions of hepatocytes, non-hepatocytes or both. Further, Notch signaling requires physical contact between signal-sending (Notch ligand-positive) and signal-receiving (Notch receptor-positive) cells, with autocrine ligand-receptor interactions unlikely due to spatial considerations, and the fact that Notch ligands inhibit Notch receptor expression when present in the same cell (Sprinzak 2010).

A specific increase in Jag1 expression was determined in livers of HFHC-fed mice. Hepatocytes and non-hepatocytes were isolated from HFHC-fed (and chow-fed control) mice by differential centrifugation and a specific increase in Jag1 was determined in hepatocytes (FIG. 9a), without significant change in other ligands. Similar increase in Jag1 expression with hyperglycemia in endothelial cells was also determined, resulting in altered Notch-mediated angiogenesis (Yoon 2013), suggesting that metabolic control of Jag1 expression can affect Notch activity. Of note, Jag1 is the most highly expressed Notch ligand in both mouse and human liver (FIGS. 9b, c) (Valenti 2013).

Staining pre- and post-intervention liver sections from OCA-responders and controls, determines higher Notch activity in NASH reflects both hepatocyte and non-hepatocyte contributions, and hepatic JAG1 expression and staining in hepatocytes predicts altered HES1/HEYL and NASH activity.

In addition, laser-capture microdissection followed by RNA-Seq to isolate and molecularly profile "Notch-on" hepatocytes and non-hepatocytes delineates these cellular populations.

Example 10A—ΔJAG1 Correlates with NASH Improvement qPCR is performed from paired baseline and 72 wk cDNA derived from FLINT biopsies to determine JAG1 expression in responders and non-responders, using farnesoid X receptor (FXR) target expression as a positive control for OCA-treatment. Correlation of ΔJAG1 from baseline to 72 wk with ΔHESL/HEYL expression, and ΔNAS and ΔALT is determined as described in Example 9. As a negative control, the same analysis is determined with other Notch ligands (DLL4) which do not change in PIVENS.

Staining formalin-fixed liver sections from research subjects of the FLINT trial is performed to determine which cells in liver express JAG1. Liver sections from all cases have been previously stained with H&E and Masson's trichrome stain to assess for NASH pathology (Kleiner 2005), but additional sections were left unstained for Ancillary Studies. To determine which liver cell(s) express JAG1, baseline and 72 wk liver sections from OCA-responders, BMI/pathology-matched OCA-treated non-responders and placebo-treated subjects (n=10/group) with anti-JAG1 are deparaffinized, rehydrated and stained, followed by detection with anti-rabbit Alexa Fluor 488 and immediate image capture with a Nikon ECLIPSE E800 microscope and a Nikon DXM 1200 digital camera (Valenti 2013). Subsets of these sections are co-stained for hepatocyte (anti-HNF4a) and non-hepatocyte (anti-CD68 for macrophages, anti-CD31 for endothelial cells, anti-SMA for HSCs and anti-CK19 for cholangiocytes) markers. These individual antibodies are used to stain human liver sections, alone and in various combinations with anti-JAG1. After image processing with Image ProPlus software, stained liver sections are quantitated from 1 (low expression) to 4 (high expression), in hepatocytes or non-hepatocytes while blinded to group assignment. Change in hepatocyte JAG1 score from baseline to 72 wk is determined, and correlated with ΔJAG1, ΔHES1 and ΔHEYL gene expression, as well as change in NASH pathology by ΔNAS and ΔALT.

In OCA-treated responders, liver JAG1 gene expression and hepatocyte JAG1 protein staining is lower at end-of-treatment as compared to baseline, and ΔJAG1 correlates with change in liver HES1 and HEYL gene expression, as well as markers of NASH activity. Change in hepatic JAG1 expression (ΔJAG1) correlates with measures of NASH improvement, and Notch activity in hepatocytes and non-hepatocytes is driven by hepatocyte JAG1.

Liver JAG1 expression and hepatocyte JAG1 staining correlates with hepatic Notch activity, as assessed by both HES1 and HEYL expression, as well as the primary outcome in FLINT. Example 10B—Characterization of JAG1+, HES1+, and HEYL+ cells in liver Hepatic HES1 and HEYL levels are stained and quantitated using the methods described in Example 9, in pre- and post-intervention liver sections from OCA-responders as well as appropriate controls (OCA- and placebo-treated non-responders). HES1 and HEYL mark Notch activation in hepatocytes and non-hepatocytes, respectively, are evaluated as described above in murine liver. HES1+/total hepatocytes (% HES1+ hepatocytes), HEYL+/total non-hepatocytes (% HEYL+ non-hepatocytes), and vice versa, are determined and compared to hepatic HES1/HEYL gene expression and change in NASH activity in these same research subjects. Quantitation for this cell type, i.e., % HEYL+ macrophages, are repeated if co-stains determine that either HES1 or HEYL marks a specific non-hepatocyte population.

Subpopulations of Notch-active and -inactive hepatocytes and non-hepatocytes, are identified consistent with the phenomenon of Notch-mediated lateral inhibition in normal development (Shawber 2004) whereby neighboring cells compete for a cell fate, producing a characteristic salt-and-pepper pattern of Notch receptor/target(+) and Notch ligand (+) cells (Axelrod 2010).

"Notch-on" cells have a distinct molecular signature as compared to "Notch-off" cells. This is causative to NASH pathology, in terms of hepatocellular damage as well as inflammation and fibrosis. Laser-capture microdissection (LCM) is performed to isolate Notch active vs. non-active hepatocytes, and similarly for distinct non-hepatocyte populations which are ascertained by HEYL staining. LCM protocols (Espine 2006) are adapted for deparaffinized and stained mouse and human liver sections, to identify and isolate hepatocyte and various liver non-hepatocyte populations (Marko-Varga 2003). An inverted Zeiss AxioObserver.Z1 microscope and a non-contact laser catapulting are use to determine higher HES1 expression in HES1+/HNF4α+ double-positive than HES1-hepatocytes in the same hepatic zone (Jungermann 1992). Similar data is observed in the HEYL+ non-hepatocyte population. This technique is applied to FLINT samples, for a molecular profiling experiment in OCA responders as compared to non-responders. Isolation of rRNA-depleted total RNA from HES1+ and HES1-hepatocytes and HEYL+ and HEYL-nonhepatocytes is achieved using TruSeq Stranded Total RNA with Ribo-Zero Gold (Illumina), and is amplified and subject to RNA-Seq, followed by Ingenuity Pathway Analysis (Qiagen) to identify the molecular repercussion of Notch activation in human liver cells in NASH.

In OCA-treated responders, hepatocyte HES1 and non-hepatocyte HEYL staining is lower at end-of-treatment as compared to baseline, correlate with change in NASH activity, and mark a distinct Notch-active cell population.

Higher Notch activity in NASH reflects both hepatocyte and non-hepatocyte contributions, and that "Notch-on", HES1+ hepatocytes and HEYL+ non-hepatocytes have a distinct molecular signature as compared to "Notch-off" control cells.

Example 11

JAG1 Expression Predicts NASH Outcomes

Analysis of PIVENS, demonstrated that high baseline hepatic JAG1 expression was associated with favorable therapeutic outcome. Baseline JAG1 expression is higher in FLINT responders which further demonstrates the clinical utility of JAG1 expression as a predictor of clinical outcome.

Example 11A—JAG1-High Patients are Responders

Using samples from the FLINT trial, JAG1 is demonstrated to correlate with likelihood of therapeutic efficacy.

qPCR is performed from cDNA derived from baseline FLINT biopsies to determine JAG1 expression. The >1.5 fg JAG1/ng 18S cutoff is tested to ensure subjects met the FLINT primary outcome. All responders (placebo+OCA) as well as OCA-responders are considered separately. As DLL4 did not significantly change in PIVENS, nor did its expression predict PIVENS response, DLL4 is used as a negative control.

JAG1-high patients are more likely to respond in FLINT. Baseline JAG1-high patients are more likely to meet the primary outcome of FLINT, regardless of treatment group, than patients with JAG1 expression of ≤1.5 fg/ng 18S.

REFERENCES

1. Savage, D. B. & Semple, R. K. Recent insights into fatty liver, metabolic dyslipidaemia and their links to insulin resistance. *Current opinion in lipidology* 21, 329-336 (2010).
2. Lin, H. V. & Accili, D. Hormonal regulation of hepatic glucose production in health and disease. *Cell metabolism* 14, 9-19 (2011).
3. Li, S., Brown, M. S. & Goldstein, J. L. Bifurcation of insulin signaling pathway in rat liver: mTORC1 required for stimulation of lipogenesis, but not inhibition of gluconeogenesis. *Proceedings of the National Academy of Sciences of the United States of America* 107, 3441-3446 (2010).
4. Bugianesi, E., et al. Insulin resistance in non-diabetic patients with non-alcoholic fatty liver disease: sites and mechanisms. *Diabetologia* 48, 634-642 (2005).
5. Dongiovanni, P., Anstee, Q. M. & Valenti, L. Genetic Predisposition in NAFLD and NASH: Impact on Severity of Liver Disease and Response to Treatment. *Curr Pharm Des* (2013).
6. Bhala, N., Jouness, R. I. & Bugianesi, E. Epidemiology and Natural History of Patients with NAFLD. *Curr Pharm Des* (2013).
7. Younossi, Z. M., et al. Changes in the prevalence of the most common causes of chronic liver diseases in the United States from 1988 to 2008. *Clin Gastroenterol Hepatol* 9, 524-530 e521; quiz e560 (2011).
8. Loria, P., et al. Practice guidelines for the diagnosis and management of nonalcoholic fatty liver disease. A decalogue from the Italian Association for the Study of the Liver (AISF) Expert Conmmittee. *Dig Liver Dis* 42, 272-282 (2010).
9. Malik, R., et al. The clinical utility of biomarkers and the nonalcoholic steatohepatitis CRN liver biopsy scoring system in patients with nonalcoholic fatty liver disease. *J Gastroenterol Hepatol* 24, 564-568 (2009).
10. Hashimoto, E. & Farrell, G. C. Will non-invasive markers replace liver biopsy for diagnosing and staging fibrosis in non-alcoholic steatohepatitis? *J Gastroenterol Hepatol* 24, 501-503 (2009).
11. Tilg, H. & Moschen, A. R. Evolution of inflammation in nonalcoholic fatty liver disease: the multiple parallel hits hypothesis. *Hepatology* 52, 1836-1846 (2010).
12. Day, C. P. & James, O. F. Steatohepatitis: a tale of two "hits" ?*Gastroenterology* 114, 842-845 (1998).
13. Nakagawa, H. Recent advances in mouse models of obesity- and nonalcoholic steatohepatitis-associated hepatocarcinogenesis. *World journal of hepatology* 7, 2110-2118 (2015).
14. Tariq, Z., Green, C. J. & Hodson, L. Are oxidative stress mechanisms the common denominator in the progression from hepatic steatosis towards non-alcoholic steatohepatitis (NASH)?*Liver Int* 34, e180-190 (2014).
15. Carpino, G., Renzi, A., Onori, P. & Gaudio, E. Role of hepatic progenitor cells in nonalcoholic fatty liver disease development: cellular cross-talks and molecular networks. *Int J Mol Sci* 14, 20112-20130 (2013).
16. Bolos, V., Grego-Bessa, J. & de la Pompa, J. L. Notch signaling in development and cancer. *Endocrine reviews* 28, 339-363 (2007).
17. Oka, C., et al. Disruption of the mouse RBP-J kappa gene results in early embryonic death. *Development* 121, 3291-3301 (1995).
18. De Strooper, B. Nicastrin: gatekeeper of the gamma-secretase complex. *Cell* 122, 318-320 (2005).
19. Pajvani, U. B., et al. Inhibition of Notch signaling ameliorates insulin resistance in a FoxO1-dependent manner. *Nature medicine* 17, 961-967 (2011).
20. Dufraine, J., Funahashi, Y. & Kitajewski, J. Notch signaling regulates tumor angiogenesis by diverse mechanisms. *Oncogene* 27, 5132-5137 (2008).
21. Funahashi, Y., et al. A notch1 ectodomain construct inhibits endothelial notch signaling, tumor growth, and angiogenesis. *Cancer research* 68, 4727-4735 (2008).
22. Funahashi, Y., et al. Notch modulates VEGF action in endothelial cells by inducing Matrix Metalloprotease activity. *Vascular cell* 3, 2 (2011).
23. Pajvani, U. B., et al. Inhibition of Notch uncouples Akt activation from hepatic lipid accumulation by decreasing mTorc1 stability. *Nature medicine* 19, 1054-1060 (2013).
24. Fukuda, D., et al. Notch ligand Delta-like 4 blockade attenuates atherosclerosis and metabolic disorders. *Pro-*

25. Li, H., Lee, J., He, C., Zou, M. H. & Xie, Z. Suppression of mTORC1/STAT3/Notch1 pathway by activated AMPK prevents hepatic insulin resistance induced by excess amino acids. *American journal of physiology. Endocrinology and metabolism* (2013).
26. Aster, J. C. & Blacklow, S. C. Targeting the Notch pathway: twists and turns on the road to rational therapeutics. *Journal of clinical oncology: official journal of the American Society of Clinical Oncology* 30, 2418-2420 (2012).
27. Espinoza, I. & Miele, L. Notch inhibitors for cancer treatment. *Pharmacol Ther* 139, 95-110 (2013).
28. Yan, M. Therapeutic promise and challenges of targeting DLL4/NOTCH1. *Vascular cell* 3, 17 (2011).
29. Gawrieh, S. & Chalasani, N. Pharmacotherapy for Nonalcoholic Fatty Liver Disease. *Semin Liver Dis* 35, 338-348 (2015).
30. Ratziu, V., Goodman, Z. & Sanyal, A. Current efforts and trends in the treatment of NASH. *Journal of hepatology* 62, S65-75 (2015).
31. Valenti, L., et al. Hepatic Notch Signaling Correlates with Insulin Resistance and Non-Alcoholic Fatty Liver Disease. *Diabetes* (2013).
32. Yilmaz, Y. Review article: is non-alcoholic fatty liver disease a spectrum, or are steatosis and non-alcoholic steatohepatitis distinct conditions? *Aliment Pharmacol Ther* 36, 815-823 (2012).
33. Nijjar, S. S., Crosby, H. A., Wallace, L., Hubscher, S. G. & Strain, A. J. Notch receptor expression in adult human liver: a possible role in bile duct formation and hepatic neovascularization. *Hepatology* 34, 1184-1192 (2001).
34. Nijjar, S. S., Wallace, L., Crosby, H. A., Hubscher, S. G. & Strain, A. J. Altered Notch ligand expression in human liver disease: further evidence for a role of the Notch signaling pathway in hepatic neovascularization and biliary ductular defects. *The American journal of pathology* 160, 1695-1703 (2002).
35. Kohler, C., et al. Expression of Notch-1 and its ligand Jagged-1 in rat liver during liver regeneration. *Hepatology* 39, 1056-1065 (2004).
36. Wang, L., et al. Disruption of the transcription factor recombination signal-binding protein-Jkappa (RBP-J) leads to veno-occlusive disease and interfered liver regeneration in mice. *Hepatology* 49, 268-277 (2009).
37. Fortini, M. E. & Bilder, D. Endocytic regulation of Notch signaling. *Current opinion in genetics & development* 19, 323-328 (2009).
38. Axelrod, J. D. Delivering the lateral inhibition punchline: it's all about the timing. *Science signaling* 3, pe38 (2010).
39. Baratta, J. L., et al. Cellular organization of normal mouse liver: a histological, quantitative immunocytochemical, and fine structural analysis. *Histochem Cell Biol* 131, 713-726 (2009).
40. van Rooijen, N. & Hendrikx, E. Liposomes for specific depletion of macrophages from organs and tissues. *Methods in molecular biology* 605, 189-203 (2010).
41. Huang, W., et al. Depletion of liver Kupffer cells prevents the development of diet-induced hepatic steatosis and insulin resistance. *Diabetes* 59, 347-357 (2010).
42. Bataller, R. & Brenner, D. A. Hepatic stellate cells as a target for the treatment of liver fibrosis. *Semin Liver Dis* 21, 437-451 (2001).
43. Sawitza, I., Kordes, C., Reister, S. & Haussinger, D. The niche of stellate cells within rat liver. *Hepatology* 50, 1617-1624 (2009).
44. Mederacke, I., et al. Fate tracing reveals hepatic stellate cells as dominant contributors to liver fibrosis independent of its aetiology. *Nat Commun* 4, 2823 (2013).
45. Baron, M. Endocytic routes to Notch activation. *Semin Cell Dev Biol* 23, 437-442 (2012).
46. Rinella, M. E. & Green, R. M. The methionine-choline deficient dietary model of steatohepatitis does not exhibit insulin resistance. *Journal of hepatology* 40, 47-51 (2004).
47. Kohli, R. & Feldstein, A. E. NASH animal models: are we there yet? *Journal of hepatology* 55, 941-943 (2011).
48. Rinella, M. E., et al. Mechanisms of hepatic steatosis in mice fed a lipogenic methionine choline-deficient diet. *Journal of lipid research* 49, 1068-1076 (2008).
49. Kohli, R., et al. High-fructose, medium chain trans fat diet induces liver fibrosis and elevates plasma coenzyme Q9 in a novel murine model of obesity and nonalcoholic steatohepatitis. *Hepatology* 52, 934-944 (2010).
50. Ibrahim, S. H., et al. Mixed lineage kinase 3 deficient mice are protected against the high fat high carbohydrate diet-induced steatohepatitis. *Liver Int* (2013).
51. Schuler, M., Dierich, A., Chambon, P. & Metzger, D. Efficient temporally controlled targeted somatic mutagenesis in hepatocytes of the mouse. *Genesis* 39, 167-172 (2004).
52. Chartoumpekis, D. V., et al. Notch intracellular domain overexpression in adipocytes confers lipodystrophy in mice. *Molecular metabolism* 4, 543-550 (2015).
53. Chen, F., et al. Nicastrin binds to membrane-tethered Notch. *Nature cell biology* 3, 751-754 (2001).
54. Kleiner, D. E., et al. Design and validation of a histological scoring system for nonalcoholic fatty liver disease. *Hepatology* 41, 1313-1321 (2005).
55. Sanyal, A. J., et al. Endpoints and clinical trial design for nonalcoholic steatohepatitis. *Hepatology* 54, 344-353 (2011).
56. Sanyal, A. J., et al. Pioglitazone, vitamin E, or placebo for nonalcoholic steatohepatitis. *The New England journal of medicine* 362, 1675-1685 (2010).
57. Chalasani, N. P., et al. Pioglitazone versus vitamin E versus placebo for the treatment of non-diabetic patients with non-alcoholic steatohepatitis: PIVENS trial design. *Contemporary clinical trials* 30, 88-96 (2009).
58. Neuschwander-Tetri, B. A., et al. Farnesoid X nuclear receptor ligand obeticholic acid for non-cirrhotic, non-alcoholic steatohepatitis (FLINT): a multicentre, randomised, placebo-controlled trial. *Lancet* 385, 956-965 (2015).
59. Teodoro, J. S., Rolo, A. P. & Palmeira, C. M. Hepatic FXR: key regulator of whole-body energy metabolism. *Trends in endocrinology and metabolism: TEM* 22, 458-466 (2011).
60. Sprinzak, D., et al. Cis-interactions between Notch and Delta generate mutually exclusive signalling states. *Nature* 465, 86-90 (2010).
61. Yoon, C. H., et al. High glucose-induced jagged 1 in endothelial cells disturbs notch signaling for angiogenesis: A novel mechanism of diabetic vasculopathy. *J Mol Cell Cardiol* (2013).
62. Shawber, C. J. & Kitajewski, J. Notch function in the vasculature: insights from zebrafish, mouse and man. *BioEssays: news and reviews in molecular, cellular and developmental biology* 26, 225-234 (2004).

63. Espina, V., Milia, J., Wu, G., Cowherd, S. & Liotta, L. A. Laser capture microdissection. *Methods in molecular biology* 319, 213-229 (2006).
64. Espina, V., et al. Laser-capture microdissection. *Nature protocols* 1, 586-603 (2006).
65. Marko-Varga, G., Berglund, M., Malmstrom, J., Lindberg, H. & Fehniger, T. E. Targeting hepatocytes from liver tissue by laser capture microdissection and proteomics expression profiling. *Electrophoresis* 24, 3800-3805 (2003).
66. Sozer, S. & Hoffman, R. Laser-capture microdissection and analysis of liver endothelial cells from patients with Budd-Chiari syndrome. *Methods in molecular biology* 755, 405-415 (2011).
67. Kandathil, A. J., et al. Use of laser capture microdissection to map hepatitis C virus-positive hepatocytes in human liver. *Gastroenterology* 145, 1404-1413 e1401-1410 (2013).
68. Jungermann, K. Role of intralobular compartmentation in hepatic metabolism. *Diabete Metab* 18, 81-86 (1992).
69. Jungermann, K. & Thurman, R. G. Hepatocyte heterogeneity in the metabolism of carbohydrates. *Enzyme* 46, 33-58 (1992).
70. Guy, C. D., et al. Treatment response in the PIVENS trial is associated with decreased Hedgehog pathway activity. *Hepatology* 61, 98-107 (2015).
71. Kangsamaksin, T., et al. NOTCH decoys that selectively block DLL/NOTCH or JAG/NOTCH disrupt angiogenesis by unique mechanisms to inhibit tumor growth. *Cancer discovery* 5, 182-197 (2015).
72. Banerjee, D., et al. Notch suppresses angiogenesis and progression of hepatic metastases. *Cancer research* 75, 1592-1602 (2015).
73. Takebe, N., Nguyen, D. & Yang, S. X. Targeting Notch signaling pathway in cancer: Clinical development advances and challenges. *Pharmacol Ther* 141, 140-149 (2014).
74. Loomba, R., et al. Magnetic resonance elastography predicts advanced fibrosis in patients with nonalcoholic fatty liver disease: a prospective study. *Hepatology* 60, 1920-1928 (2014).
75. Verna, E. C., et al. Novel association between serum pentraxin-2 levels and advanced fibrosis in well-characterised patients with non-alcoholic fatty liver disease. *Aliment Pharmacol Ther* 42, 582-590 (2015).
76. Cui, J., et al. Comparative diagnostic accuracy of magnetic resonance elastography vs. eight clinical prediction rules for non-invasive diagnosis of advanced fibrosis in biopsy-proven non-alcoholic fatty liver disease: a prospective study. *Aliment Pharmacol Ther* 41, 1271-1280 (2015).
77. Fernandez, M., et al. Transient elastography using Fibroscan is the most reliable noninvasive method for the diagnosis of advanced fibrosis and cirrhosis in alcoholic liver disease. *Eur J Gastroenterol Hepatol* 27, 1074-1079 (2015).
78. Vuppalanchi, R. & Sanyal, A. J. Myths and mysteries about staging hepatic fibrosis by fibroscan. *Clin Gastroenterol Hepatol* 13, 780-782 (2015).
79. Castera, L., Vilgrain, V. & Angulo, P. Noninvasive evaluation of NAFLD. *Nat Rev Gastroenterol Hepatol* 10, 666-675 (2013).
80. Petta, S., et al. The combination of liver stiffness measurement and NAFLD fibrosis score improves the noninvasive diagnostic accuracy for severe liver fibrosis in patients with nonalcoholic fatty liver disease. *Liver Int* 35, 1566-1573 (2015).
81. Kwok, R., et al. Screening diabetic patients for non-alcoholic fatty liver disease with controlled attenuation parameter and liver stiffness measurements: a prospective cohort study. *Gut* (2015).
82. Noureddin, M., et al. Utility of magnetic resonance imaging versus histology for quantifying changes in liver fat in nonalcoholic fatty liver disease trials. *Hepatology* 58, 1930-1940 (2013).
83. Le, T. A., et al. Effect of colesevelam on liver fat quantified by magnetic resonance in nonalcoholic steatohepatitis: a randomized controlled trial. *Hepatology* 56, 922-932 (2012).
84. Sasso, M., et al. Novel controlled attenuation parameter for noninvasive assessment of steatosis using Fibroscan®: validation in chronic hepatitis C. *J Viral Hepat* 19, 244-253 (2012).
85. Morling, J. R., et al. Non-invasive hepatic biomarkers (ELF and CK18) in people with type 2 diabetes: the Edinburgh type 2 diabetes study. *Liver Int* 34, 1267-1277 (2014).
86. Lavine, J. E., et al. Effect of vitamin E or metformin for treatment of nonalcoholic fatty liver disease in children and adolescents: the TONIC randomized controlled trial. *JAMA: the journal of the American Medical Association* 305, 1659-1668 (2011).
87. Bell, L. N., et al. Relationship between adipose tissue insulin resistance and liver histology in nonalcoholic steatohepatitis: a pioglitazone versus vitamin E versus placebo for the treatment of nondiabetic patients with nonalcoholic steatohepatitis trial follow-up study. *Hepatology* 56, 1311-1318 (2012).
88. Morling, J. R., et al. Using non-invasive biomarkers to identify hepatic fibrosis in people with type 2 diabetes mellitus: the Edinburgh type 2 diabetes study. *Journal of hepatology* 60, 384-391 (2014).
89. Satapathy, S. K. & Sanyal, A. J. Epidemiology and Natural History of Nonalcoholic Fatty Liver Disease. *Semin Liver Dis* 35, 221-235 (2015).
90. Wang, Y. C., McPherson, K., Marsh, T., Gortmaker, S. L. & Brown, M. Health and economic burden of the projected obesity trends in the USA and the UK. *Lancet* 378, 815-825 (2011).

What is claimed:

1. A method of treating a subject afflicted with a nonalcoholic fatty liver disease and identified as a predicted responder to a pharmaceutical composition known for treating such disease which comprises administering to the subject a therapeutically effective amount of such pharmaceutical composition, wherein the subject is identified as a predicted responder when the subject's JAG1 expression level is greater than 1.5 fg/ng 18S.

2. The method of claim 1, wherein the subject's HES1 expression level is greater than 1.5 fg/ng 18S.

3. The method of claim 1, wherein the subject's HEYL expression level is greater than 1.5 fg/ng 18S.

4. The method of claim 2, wherein the subject's HEYL expression level is greater than 1.5 fg/ng 18S.

5. The method of claim 1, wherein the pharmaceutical composition comprises vitamin E, selenium, betadine, metformin, rosiglitazone, piogliatazone, insulin sensitizers, antioxidants, probiotics, Omega-3 DHA, pentoxifylline, anti-TNF-alpha, FXR agonists, GLP-1 agonist, or obeticholic acid.

6. The method of claim 5, wherein the pharmaceutical composition comprises vitamin E, piogliatazone, or obeticholic acid.

7. The method of claim 1, wherein the pharmaceutical composition comprises a Notch inhibitor.

8. The method of claim 1, wherein the nonalcoholic fatty liver disease is nonalcoholic steatohepatitis.

9. A method of treating a subject afflicted with a nonalcoholic fatty liver disease and identified as a predicted responder to a pharmaceutical composition comprising a Notch inhibitor which comprises administering to the subject a therapeutically effective amount of such pharmaceutical composition, wherein the subject is identified as a predicted responder when the subject's JAG1 expression level is greater than 1.5 fg/ng 18S.

10. The method of claim 9, wherein the subject's HES1 expression level is greater than 1.5 fg/ng 18S.

11. The method of claim 9, wherein the subject's HEYL expression level is greater than 1.5 fg/ng 18S.

12. The method of claim 10, wherein the subject's HEYL expression level is greater than 1.5 fg/ng 18S.

13. The method of claim 9, wherein the nonalcoholic fatty liver disease is nonalcoholic steatohepatitis.

14. A method of treating a subject afflicted with a nonalcoholic fatty liver disease and identified as a predicted responder to a pharmaceutical composition comprising vitamin E, piogliatazone, or obeticholic acid which comprises administering to the subject a therapeutically effective amount of such pharmaceutical composition, wherein the subject is identified as a predicted responder when the subject's JAG1 expression level is greater than 1.5 fg/ng 18S.

\* \* \* \* \*